(12) United States Patent
Mak et al.

(10) Patent No.: US 12,060,440 B2
(45) Date of Patent: *Aug. 13, 2024

(54) CYCLOPHILIN INHIBITORS AND USES THEREOF

(71) Applicant: Farsight Medical Technology (Shanghai) Co., Ltd., Shanghai (CN)

(72) Inventors: Ching-Pong Mak, Shanghai (CN); Hans Fliri, Shanghai (CN); Fashu Ma, Shanghai (CN); Michael Peel, Shanghai (CN)

(73) Assignee: FARSIGHT MEDICAL TECHNOLOGY (SHANGHAI) CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/946,071

(22) Filed: Sep. 16, 2022

(65) Prior Publication Data

US 2023/0110497 A1 Apr. 13, 2023

Related U.S. Application Data

(63) Continuation of application No. PCT/CN2021/083013, filed on Mar. 25, 2021.

(30) Foreign Application Priority Data

Mar. 26, 2020 (WO) ................ PCT/CN2020/081295
Mar. 1, 2021 (WO) ................ PCT/CN2021/078391

(51) Int. Cl.
*C07K 7/64* (2006.01)
*A61P 37/00* (2006.01)

(52) U.S. Cl.
CPC ................ *C07K 7/64* (2013.01); *A61P 37/00* (2018.01); *C07K 7/645* (2013.01)

(58) Field of Classification Search
None
See application file for complete search history.

(56) References Cited

U.S. PATENT DOCUMENTS

| | | | |
|---|---|---|---|
| 6,583,265 B1 | 6/2003 | Ellmerer-Mueller et al. | |
| 6,809,077 B2 | 10/2004 | Or et al. | |
| 8,481,483 B2 | 7/2013 | Or et al. | |
| 2013/0210704 A1 | 8/2013 | Su et al. | |
| 2013/0303438 A1* | 11/2013 | Su .......................... | A61P 31/20 530/321 |
| 2020/0085825 A1 | 3/2020 | Kissel et al. | |

FOREIGN PATENT DOCUMENTS

| | | |
|---|---|---|
| CN | 101068829 A | 11/2007 |
| CN | 101511357 A | 8/2009 |
| CN | 104768968 A | 7/2015 |
| CN | 104870007 A | 8/2015 |
| CN | 106902346 A | 6/2017 |
| CN | 106902347 A | 6/2017 |
| CN | 109476705 A | 3/2019 |
| CN | 111449050 A | 7/2020 |
| EP | 0194972 A2 | 9/1986 |
| EP | 0484281 A2 | 5/1992 |
| EP | 2751127 B1 | 7/2016 |
| WO | 9965933 A1 | 12/1999 |
| WO | 03033010 A1 | 4/2003 |
| WO | 2004082629 A2 | 9/2004 |
| WO | 2006039668 A2 | 4/2006 |
| WO | WO 2006/039668 * | 4/2006 |
| WO | 2008143996 A1 | 11/2008 |
| WO | 2010012073 A1 | 2/2010 |
| WO | 2012079172 A1 | 6/2012 |
| WO | 2016027089 A1 | 2/2016 |
| WO | 2017200984 A1 | 11/2017 |
| WO | 2019016572 A1 | 1/2019 |
| WO | 2020038426 A1 | 2/2020 |
| WO | 2020147624 A1 | 7/2020 |

OTHER PUBLICATIONS

Mayo Clinic (downloaded online from URL :<http://www.mayoclinic.com/health/epidermolysis-bullosa/DS01015>) (Year: 2024).*
CIDRAP News (Year: 2003).*
Hersh et al., Clinical Infectious Diseases 2012;54(11):1677-8 (Year: 2012).*
NPR, Transplant agency is criticized for donor organs arriving late, damaged or diseased, Aug. 17, 2022 (Year: 2022).*
Written Opinion of International Application No. PCT/CN2021/083016, 6 pages.
Written Opinion of the International Application No. PCT/CN2020/081296, 6 pages.
Written Opinion of International Application No. PCT/CN2021/083015, 7 pages.
Written Opinion of the International Application No. PCT/CN2020/081295, 7 pages.
Written Opinion of the International Application No. PCT/CN2021/083013, 8 pages.
Devalaraja-Narashimha, Kishor , et al., "Cyclophilin D gene ablation protects mice from ischemic renal injury", Am J Physiol Renal Physiol, vol. 297, Jun. 24, 2009, pp. 749-759.
Klawitter, Jelena , et al., "Cyclophilin D knockout protects the mouse kidney against cyclosporin A-induced oxidative stress", Am J Physiol Renal Physiol; vol. 317, Jun. 12, 2019, pp. 683-694.

* cited by examiner

*Primary Examiner* — Sergio Coffa
(74) *Attorney, Agent, or Firm* — Pharma Patents International AG; Lily Ackerman

(57) ABSTRACT

Compounds defined by Formula 4 are used as cyclophilin inhibitors for the prevention or treatment of diseases or disorders, such as organ injury or organ failure.

3 Claims, No Drawings

CYCLOPHILIN INHIBITORS AND USES THEREOF

CROSS REFERENCE TO RELATED APPLICATIONS

This application is a continuation of International Application No. PCT/CN2021/083013, filed on Mar. 25, 2021, which claims priority to and the benefit of International Application No. PCT/CN2021/078391, filed on Mar. 1, 2021, and International Application No. PCT/CN2020/081295, filed on Mar. 26, 2020, all of which are incorporated herein by reference in their entireties.

BACKGROUND OF THE INVENTION

The present invention relates to cyclosporin analogues, and their use for the treatment or prevention of disease or disorders, in particular disease or conditions associated with cellular injury or cell death, which can be caused by a number of different reasons, such as ischemia or ischemia reperfusion injury, toxins, infection or mechanical trauma. In particular, the invention relates to compounds which may be provided as potent cyclophilin D inhibitors.

Acute inflammation is well recognized to involve the complex interaction of various cellular (neutrophils, macrophages) and extracellular (complement, histamine) factors that act in response to PAMP (pathogen-activated molecular patterns) and DAMP (damage-activated molecular patterns) signals to resolve the originating insult. Cyclophilin A has been demonstrated to function as a chemokine to facilitate leukocyte migration in support of an inflammatory response and blockade of cyclophilin A was shown to be beneficial in animal models of acute inflammation. More recently a severe form of inflammation that is accompanied by cell death and tissue necrosis has been described. A significant body of evidence now supports the opening of a pore at the mitochondrial membrane, termed the Mitochondrial Permeability Transition Pore (MPTP), as being critical to the onset and maintenance of this necrotic inflammation. A key regulator of this MPTP opening is Cyclophilin D (CypD), and inhibitors of CypD have shown good activity in preventing tissue damage associated with necrotic inflammation. Opening of the MPTP, and subsequent initiation of necrotic cell death, is triggered by elevated intracellular calcium levels that result from a variety of factors including excessive physiological signals (e.g. noise trauma, excitotoxicity), oxidative stress, hypoxia, bile salt toxins, etc. Notably, genetic ablation, or pharmacological inhibition, of CypD was found to be protective toward tissue degradation due to ischemia-reperfusion injury of cardiac tissue suggesting that CypD inhibition is a viable drug target for ischemia-reperfusion injury more generally.

In mouse models cyclophilin D deletion was shown to have a significant protective effect against damage caused to the kidney by a severe ischemia-reperfusion insult (*Am J Physiol Renal Physiol* 297: F749-F759, 2009). This protective effect was evident in improved renal function, as measured by serum creatinine levels, and in tissue damage (measured by histology) in the cyclophilin D knockout animals compared to wild type controls. Similarly, in a mouse model of kidney damage caused by administration of a nephrotoxic drug (Am J Physiol Renal Physiol. 2019 Sep. 1; 317(3):F683-F694), animals in which cyclophilin D was knocked out were more resistant to oxidative stress and hypomethylation and had lower indications of renal toxicity than wild type animals.

In studies carried out using cyclophilin D knockout mice as well as pharmacological strategies with cyclophilin inhibitors it has been unambiguously demonstrated that opening of the mitochondrial permeability transition pore (MPTP), a non-specific channel in the inner mitochondrial membrane, is a fundamental event in cell death that results from a variety of insults. Further, inhibition of cyclophilin D can prevent opening of the mPTP which is protective toward mitochondrial function and preserves cell viability.

Cyclosporin A is a compound well known for its immunosuppressive properties, but other biological properties have also been described. Cyclosporin A has the following chemical structure:

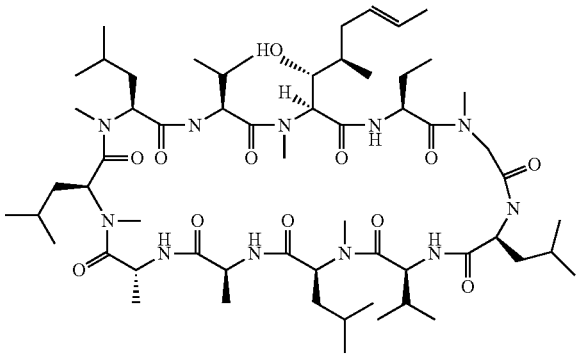

Cyclosporin A (CsA)

Biologically active derivatives of Cyclosporin A have also been made. For example, U.S. Pat. No. 6,583,265, EP0484281, EP0194972 describes cyclosporin derivatives having various properties including immunosuppressive, antiparasitic and antiviral properties. U.S. Pat. No. 6,583,265 describes cyclosporin derivatives with modifications made at position 3 of the cyclosporin macrocycle. In particular, U.S. Pat. No. 6,583,265 discloses Compound 1:

Compound 1

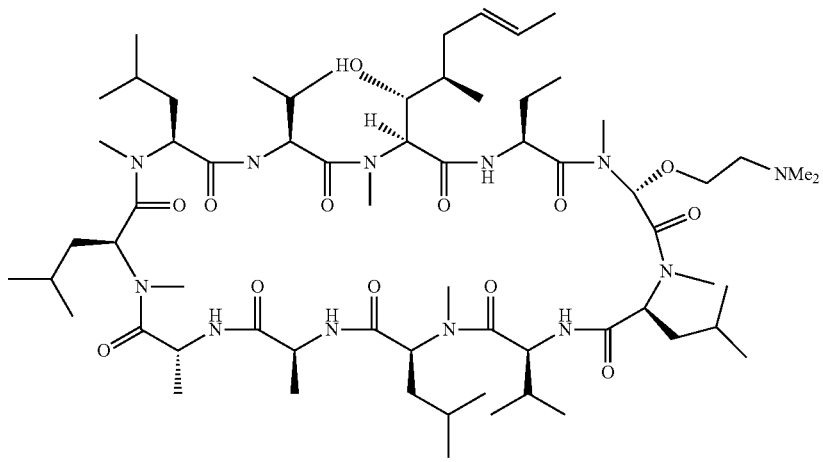

WO2019/016572 A1 also describes Compound 1 for use in the treatment or prevention of acute or chronic inflammatory disorders.

It is an object of the present invention to provide further cyclosporin analogues, in particular analogues which may be useful for inhibition of cyclophilins, e.g. cyclophilin A, B, and D, and diseases and conditions associated therewith.

Further objects of the invention will be clear on the basis of the following description of the invention, examples and claims.

SUMMARY OF THE INVENTION

In a first aspect, the invention relates to compounds as defined in the detailed description, i.e. compounds of Formula 1, Formula 2 or Formula 3, or Formula 4.

In a further aspect, the present invention provides for the use of said compounds as cyclophilin inhibitors. In yet a further aspect, the invention provides for use of said compounds in a method of preventing and/or treating diseases or condition associated with cell injury or cell death, such as organ injury or organ failure. In yet another aspect, the invention may provide for use of said compounds in the prevention and/or treatment of a kidney condition or disease in a subject exposed to a nephrotoxin capable of inducing said kidney condition or disease, wherein the nephrotoxin is a nephrotoxic drug substance or an endogenous nephrotoxin.

DETAILED DESCRIPTION OF THE INVENTION

In a first aspect, the present disclosure relates to a compound of Formula 1, or a pharmaceutically acceptable salt thereof:

(Formula 1)

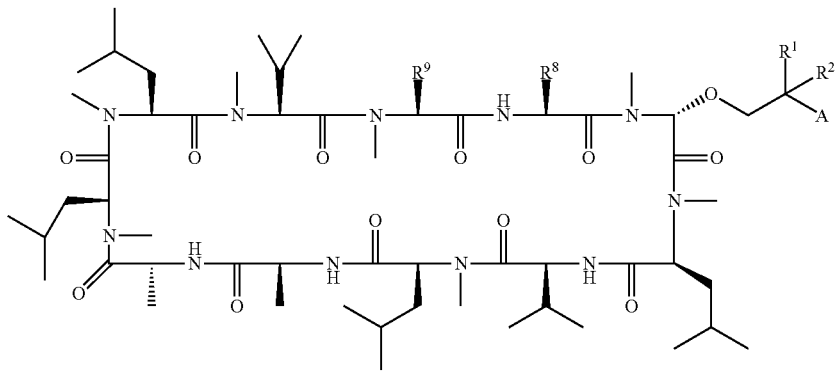

wherein:

$R^1$ and $R^2$ are independently selected from H, $C_1$ to $C_6$ alkyl or wherein $R^1$ and $R^2$ are joined together to form a $C_3$ to $C_6$ cycloalkyl or heterocycloalkyl ring;

A is selected from:

$NR^3R^4$, wherein $R^3$ and $R^4$ are independently selected from H, $C_1$ to $C_6$ alkyl, or wherein $R^3$ and $R^4$ are joined together to form a $C_3$ to $C_6$ cycloalkyl or heterocycloalkyl ring; and $N=C(R^5)NR^6R^7$, wherein $R^5$, $R^6$ and $R^7$ are independently selected from H, $C_1$ to $C_6$ alkyl, and optionally wherein $R^6$ and $R^7$ are joined together to form a $C_3$ to $C_6$ cycloalkyl or heterocycloalkyl ring;

$R^8$ is ethyl, 1-hydroxyethyl, isopropyl, or n-propyl;

$R^9$ is Formula 1a or 1b

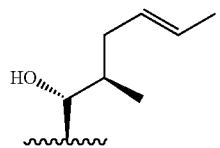
(Formula 1a)

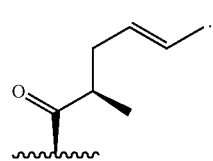
(Formula 1b)

In one embodiment, the disclosure relates to a compound of Formula 1, wherein if $R^1$ and $R^2$ are both H and $R^8$ is selected from ethyl, isopropyl, and n-propyl, $R^9$ is Formula 1a and A is $NR^3R^4$, then $R^3$ and $R^4$ are not H, $C_1$-$C_4$ alkyl, or joined together to form an azetidinyl, pyrrolidinyl, piperidinyl, piperazinyl, morpholinyl, imidazolyl, or phthaloyl residue. In a further embodiment, the disclosure relates to a compound of Formula 1, wherein if $R^1$ and $R^2$ are both H, or wherein if $R_1$ is methyl and $R_2$ is H; and $R^8$ is selected from ethyl, isopropyl, and n-propyl, $R^9$ is Formula 1a and A is $NR^3R^4$, then $R^3$ and $R^4$ are not H, $C_1$-$C_4$ alkyl, or joined together to form an azetidinyl, pyrrolidinyl, piperidinyl, piperazinyl, morpholinyl, imidazolyl, or phthaloyl residue. In another embodiment, the disclosure relates to a compound of Formula 1, wherein if $R^1$ and $R^2$ are both H, or if $R^1$ is $C_1$-$C_6$ alkyl, and $R^2$ is H, and $R^8$ is selected from ethyl, isopropyl, and n-propyl, $R^9$ is Formula 1a and A is $NR^3R^4$, then $R^3$ and $R^4$ are not H, $C_1$-$C_4$ alkyl, or joined together to form an azetidinyl, pyrrolidinyl, piperidinyl, piperazinyl, morpholinyl, imidazolyl, or phthaloyl residue. In another embodiment, the disclosure relates to a compound of Formula 1, wherein if $R^1$ and $R^2$ are both H and $R^8$ is selected from ethyl, isopropyl, and n-propyl, and $R^9$ is Formula 1a, then A is not $NR^3R^4$. In a further embodiment, the disclosure relates to a compound of Formula 1, wherein if $R^1$ and $R^2$ are both H, or if $R^1$ is $C_1$ to $C_6$ alkyl, and $R^2$ is H and $R^8$ is selected from ethyl, isopropyl, and n-propyl, and $R^9$ is Formula 1a, then A is not $NR^3R^4$.

In yet another embodiment, the disclosure relates to a compound as defined for Formula 1, provided that if $R^1$ and $R^2$ are both H and $R^8$ is selected from ethyl, then A is not $NR^3R^4$; or provided that if $R^1$ and $R^2$ are both H, or if $R^1$ is H and $R^2$ is $C_1$ to $C_6$ alkyl, and $R^8$ is selected from ethyl, and $R^9$ is Formula 1a, then A is not $NR^3R^4$. In particular, the compound of Formula 1 does not comprise Compound 1 depicted above. The compound of Formula 1 also does not comprise 3-[2-(aminopropoxy)]cyclosporin.

In a related aspect, the present disclosure may also relate to a compound, or a pharmaceutically acceptable salt thereof, of Formula 2:

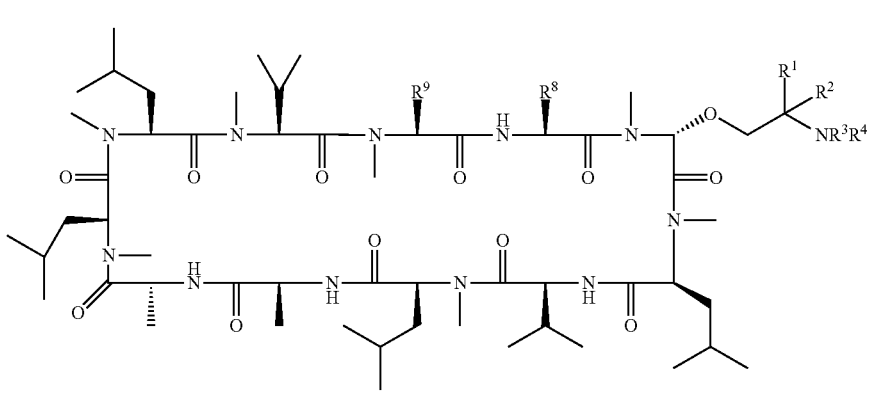
(Formula 2)

wherein:
$R^1$ and $R^2$ are independently selected from H, $C_1$ to $C_6$ alkyl, or wherein $R^1$ and $R^2$ are joined together to form a $C_3$ to $C_6$ cycloalkyl or heterocycloalkyl ring;
$R^3$ and $R^4$ are independently selected from H, $C_1$ to $C_6$ alkyl, or wherein $R^3$ and $R^4$ are joined together to form a $C_3$ to $C_6$ cycloalkyl or heterocycloalkyl ring;
$R^8$ 1-hydroxyethyl, isopropyl, or n-propyl; and
$R^9$ is Formula 1a or 1b

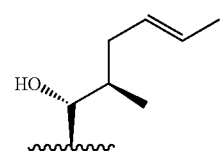
(Formula 1a)

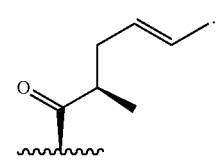
(Formula 1b)

In a related aspect, the present disclosure also may relate to a compound, or a pharmaceutically acceptable salt thereof of Formula 3:

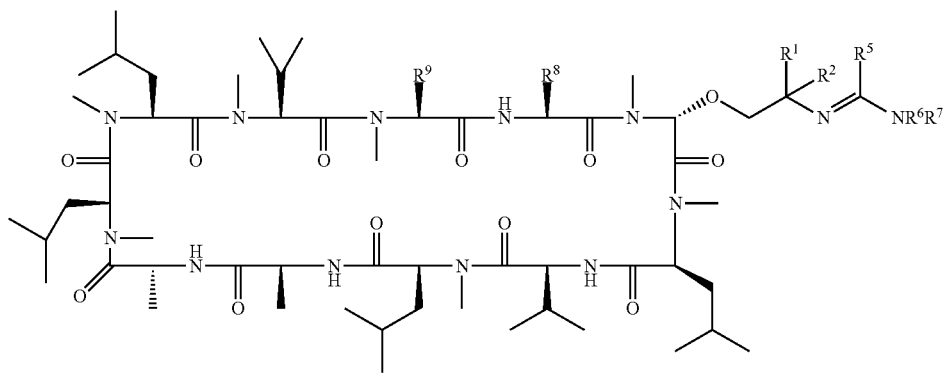

(Formula 3)

wherein:
$R^1$ and $R^2$ are independently selected from H, $C_1$ to $C_6$ alkyl, or wherein $R^1$ and $R^2$ are joined together to form a $C_3$ to $C_6$ cycloalkyl or heterocycloalkyl ring;
wherein $R^5$, $R^6$ and $R^7$ are independently selected from H, $C_1$ to $C_6$ alkyl, and optionally wherein $R^6$ and $R^7$ are joined together to form a $C_3$ to $C_6$ cycloalkyl or heterocycloalkyl ring;
$R^8$ is ethyl, 1-hydroxyethyl, isopropyl, or n-propyl; and
$R^9$ is Formula 1a or 1b

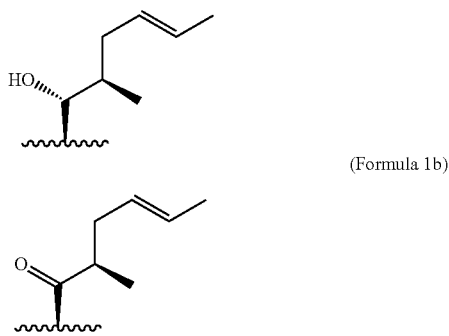

(Formula 1a)

(Formula 1b)

In particular, the compounds of Formulas 1, 2 and 3, and Formula 4 relate to cyclosporin analogues of cyclosporin A, C, D, or G.

In one embodiment, the cyclosporin compound according to the disclosure is a cyclosporin A compound (e.g. $R^9$ residue is Formula 1a, and $R^8$ is ethyl) comprising a substituent at the sarcosine residue at position 3 of the macrocyclic ring such as defined in any one, or combination of the embodiments described herein for sarcosine substituents for compounds as described herein, and of Formulas 1, 2, or 3. In other embodiments, the cyclosporin compound according to the disclosure is a cyclosporin C compound (e.g. $R^9$ residue is Formula 1a, and $R^8$ is 1-hydroxyethyl), a cyclosporin D compound (e.g. $R^9$ residue is Formula 1a, and $R^8$ is isopropyl, or a cyclosporin G compound (e.g. $R^9$ residue is Formula 1a, and $R^8$ is n-propyl), comprising a substituent at position 3, i.e. the sarcosine residue as defined for any one or combination of the embodiments described herein for compounds of Formulas, 1, 2 or 3, or Formula 4.

The position numbering as used herein refers to commonly used nomenclature and number assignment of the 11 amino acid residues featured in the cyclosporin core. With cyclosporin A as basis, the amino acids residues may be numbered as follows: methyl-butenyl-threonine, which may be abbreviated as MeBmt (1), aminobutyric acid (2)), sarcosine, which may be abbreviated as Sar (3), N-methyl leucine (4), valine (5), N-methyl leucine (6), alanine (7), D-alanine (8), N-methyl leucine (9), N-methyl leucine (10), N-methyl valine (11).

The term 'H' as used herein refers to hydrogen. The term '$C_1$ to $C_6$ alkyl' as used herein is defined as a saturated or unsaturated alkyl hydrocarbon moiety comprising 1 to 6 carbon atoms in any isomeric configuration. Included are straight-chain, linear alkyl, such as methyl, ethyl, n-propyl, n-butyl, 1-pentyl, n-hexyl. Also included are branched alkyl (i.e. branched $C_3$ to $C_6$ alkyl) such as isopropyl, sec-butyl, isobutyl, tert-butyl, 2-pentyl, 3-pentyl, isopentyl, tert-pentyl, neopentyl, and isomers of hexyl. Further included within the definition of '$C_1$ to $C_6$ alkyl' are cyclic isomers such as cyclopropyl, cyclobutyl, cyclopentyl, and cyclohexyl. Examples of unsaturated $C_1$ to $C_6$ alkyl include but are not limited to vinyl, allyl, butenyl, pentenyl, and hexenyl, and other alkenyl or alkylene moieties, for example comprising one or more double bonds e.g. pentadienyl. The term '$C_3$ to $C_6$' is to be understood analogously but denoting a moiety comprising a range of 3 to 6 carbon atoms.

In preferred embodiments, the $C_1$ to $C_6$ alkyl refers to an unsubstituted hydrocarbon moiety such as defined above. In an optional embodiment, the $C_1$ to $C_6$ alkyl may be substituted with one or more substituents, whereby one or more hydrogen atoms are replaced with a bond to said substituent or moiety other than hydrogen.

The term 'substituted' such substituted alkyl (e.g. substituted $C_1$ to $C_6$ alkyl for example) may refer to a moiety or radical, wherein one or more hydrogens are replaced, independently, with at least one or more (e.g. two, three, or more) substituents such as halogen, haloalkyl, hydroxyl (—OH), $C_1$ to $C_6$ alkoxyl, amino (—NH$_2$), monoalkylamino, dialkylamino, thioalkyl, nitro, cyano, carboxyl, alkoxycarbonyl, aryl and heteroaryl.

The term 'halogen' is interchangeable with 'halo', and may refer to chloro, bromo, iodo or fluoro atoms. 'Haloalkyl' refers to an alkyl substituent wherein one or more hydrogen atoms are replaced by one or more halogen atoms. An example of haloalkyl is trifluoroalkyl such as trifluoromethyl.

The term 'hydroxyl' refers to a —OH radical. In some embodiments, the hydrogen may be substituted, for example with a hydroxy protecting group within the art. The term 'alkoxyl' or the like means an alkylated hydroxyl substituent, i.e. in which the hydrogen is replaced by an alkyl group. '$C_1$ to $C_6$ alkoxy' refers to the replacement of hydroxy hydrogen with a $C_1$ to $C_6$ alkyl such as defined above. Examples include methoxy, isopropoxy, phenoxy, or t-butoxy.

The term 'amino' may refer to an —$NH_2$ radical. In some embodiments, the hydrogen(s) may be substituted, for example with a protecting group, or one or more further substituent such as alkyl. The term 'monoalkylamino', refers to an amino radical in which one of the hydrogens is replaced with alkyl, e.g. $C_1$ to $C_6$ alkyl such as defined above (i.e. —NHR, wherein R is alkyl). 'Dialkylamino' refers to an amino radical whereby both hydrogens are replaced independently with alkyl (i.e. —NRR', where R and R' are alkyl, which may be the same (e.g. dimethylamino), or different).

'Thioalkyl' may refer to the radical —SR", wherein R" is alkyl, e.g. $C_1$ to $C_6$ alkyl such as defined above. The term 'carboxyl' as used herein refers to the radical —C(O)—$R^a$, wherein $R^a$ may be selected from hydrogen, alkyl, aryl, hetaryl, hydroxy, alkoxy (e.g. —$OCH_3$), amino, alkylamino, dialkyl amino, thioalkyl and the like. The term 'alkoxycarbonyl' may refers to the radical —OC(O)—$R^a$, wherein $R^a$ is selected from alkyl (e.g. $C_1$ to $C_6$ alkyl, e.g. methyl), aryl, hetaryl, alkoxy, amino, alkylamino, dialkyl amino, thioalkyl, etc.

In one embodiment, at least one, or both of $R^1$ or $R^2$ of a compound as described herein, e.g. of Formula 1, Formula 2, or Formula 3, or Formula 4 is hydrogen (H). In one embodiment, at least one of $R^1$ or $R^2$ is $C_1$ to $C_6$ alkyl. In another embodiment, one or both of $R^1$ and $R^2$ are —$CH_3$ (methyl).

In some embodiments, two adjacent $R^1$ and $R^2$ substituents may be joined together so as to form a ring together, for example a $C_3$ to $C_6$ cycloalkyl ring. 'Cycloalkyl' as used herein is a saturated, or unsaturated non-aromatic hydrocarbon ring. Examples of the moieties formed by adjacent $R^1$ and $R^2$ substituents joining together to form a ring, for example a cyclopropyl, cyclobutyl, cyclopentyl, and cyclohexyl. In one embodiment, two adjacent $R^1$ and $R^2$ substituents may be joined to form a cyclopropyl ring.

The term 'hetero' when used to describe a compound or substituent means that one or more carbon atoms are replaced by a oxygen, nitrogen or sulfur atom. In further embodiments of the current disclosure, the substituents $R^1$ and $R^2$ may be joined together to form a heterocycloalkyl ring, for example a $C_3$ to $C_6$ heterocycloalkyl ring. Unless otherwise indicated, 'heterocycloalkyl' refers to a saturated, or unsaturated non-aromatic ring forming at least part of a cyclic structure and where at least one or more carbon atoms are replaced by oxygen, nitrogen or sulfur atom (and in the case of a $C_3$ to $C_6$ heterocycloalkyl comprising between 3 to 6 carbon atoms). For example, the substituents $R^1$ and $R^2$ may be joined together to form a may be a 4-, 5- or 6-member saturated, non-aromatic ring comprising at least one heteroatom. The heterocycloalkyl ring may comprise at least one heteroatom selected from O, N, or S.

The substituent $R^8$ of a compound of Formula 1, 2 or 3, or 4 may be selected from ethyl, 1-hydroxyethyl, isopropyl, and n-propyl. In one embodiment, $R^8$ is selected from the group consisting of 1-hydroxyethyl, isopropyl, and n-propyl. In another embodiment, $R^8$ is ethyl, and $R^9$ is Formula 1b.

The substituent $R^9$ at position 1 of the cyclosporin compounds of the present disclosure may correspond to Formula 1a, i.e. position 1 of the compound may correspond to the amino acid residue N-methyl-butenyl threonine or MeBmt. Alternatively, $R^9$ may correspond to an oxidized form thereof, such as depicted in Formula 1b.

In one embodiment, the substituent A of a compound according to the present disclosure may be selected from the amino radical $NR^3R^4$, wherein $R^3$ and $R^4$ are independently selected from H, $C_1$ to $C_6$ alkyl, or wherein $R^3$ and $R^4$ are joined together to form a $C_3$ to $C_6$ cycloalkyl or heterocycloalkyl ring. In one embodiment, $R^3$ and $R^4$ are both —$CH_3$ (methyl). In another embodiment, $R^3$ and $R^4$ are joined together to form a $C_3$ to $C_6$ cycloalkyl or heterocycloalkyl ring. For example, the substituents $R^3$ and $R^4$ may be joined together to form a 4-, 5- or 6-member saturated, non-aromatic ring. The cycloalkyl ring formed by adjacent $R^3$ and $R^4$ substituents joining together in the context of the compounds of the present Formulas may include, for example azetidine, pyrrolidine, or piperidine. The heterocycloalkyl ring may be a saturated, or unsaturated non-aromatic ring forming at least part of a cyclic structure, where at least one or more carbon atoms are replaced by oxygen, nitrogen or sulfur atom, in addition to the nitrogen to which $R^3$ and $R^4$ are joined to, as featured for example in Formula 1 or 2. The substituents $R^3$ and $R^4$ may be joined together to form a 4-, 5- or 6-member saturated, non-aromatic ring comprising at least one further heteroatom to the nitrogen atom to which they are joined, for example at least one further heteroatom selected from O, N, or S. In one particular embodiment, $R^3$ and $R^4$ are joined together so as to form a morpholine residue. In an optional embodiment, the cycloalkyl or heterocycloalkyl moiety formed by $R^3$ and $R^4$ may be substituted with one or more substituents such as defined above, where by one or more hydrogen atoms are replaced with a bond to said substituent.

In another embodiment, the compound according to the present disclosure comprises a substituent A, wherein A is an amidine, in particular an amidine substituent as defined by the formula —N=C($R^5$)$NR^6R^7$, wherein $R^5$, $R^6$ and $R^7$ are independently selected from H, $C_1$ to $C_6$ alkyl and optionally, substituted $C_1$ to $C_6$ alkyl.

In one embodiment thereof, $R^5$ is selected from H and $CH_3$ (methyl). The amino radical $NR^6R^7$ may be an alkyl amino radical, for example a monoalkyl amino (one of the $R^6$ or $R^7$ is hydrogen, the other $C_1$ to $C_6$ alkyl alkyl), or a dialkylamino radical wherein $R^6$ or $R^7$ are the same, or different $C_1$ to $C_6$ alkyl group. In another embodiment, $R^6$ and $R^7$ may be both methyl. In one embodiment of the compound of Formula 1, or Formula 3, or Formula 4, A is —N=C($R^5$)$NR^6R^7$ and $R^8$ is ethyl.

The compounds according to the disclosure may be selected from Compound 2, 3, 4, et seq. or a pharmaceutically acceptable salt thereof as defined in Table 1:

TABLE 1
| Compound No. | Compound Structure |
| --- | --- |
| 1 (Reference Compound) | 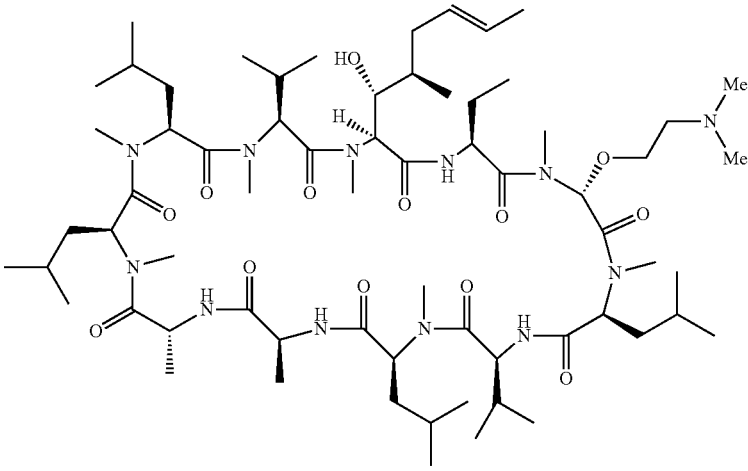 [SMILES: C/C=C/C[C@@H](C)[C@@H](O)[C@H]1C(=O)N[C@@H](CC)C(=O)N(C)[C@H](OCCN(C)C)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] |
| 2 | 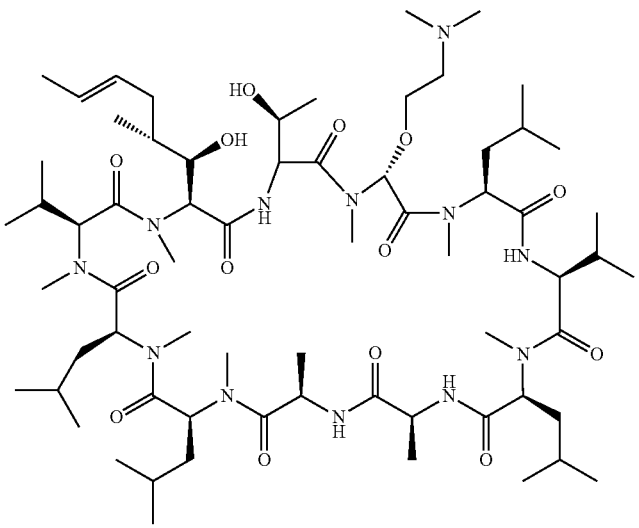 [SMILES: C/C=C/C[C@@H](C)[C@@H](O)[C@H]1C(=O)NC([C@H](C)O)C(=O)N(C)[C@H](OCCN(C)C)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] |
| 3 | 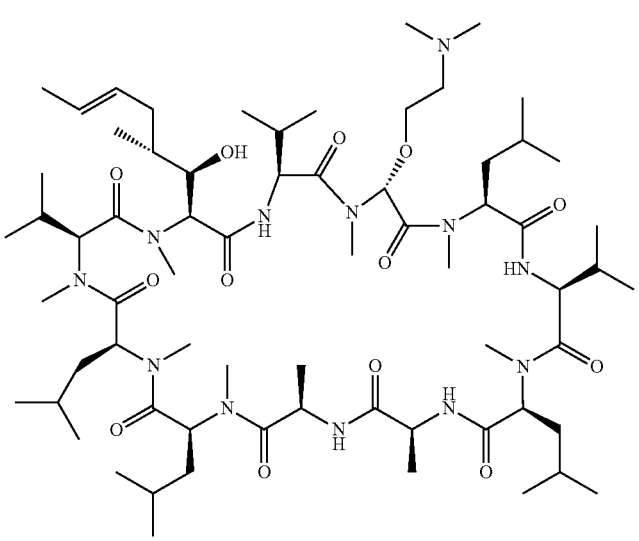 [SMILES: C/C=C/C[C@@H](C)[C@@H](O)[C@H]1C(=O)N[C@@H](C(C)C)C(=O)N(C)[C@H](OCCN(C)C)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] |

TABLE 1-continued
| Compound No. | Compound Structure |
|---|---|
| 4 | 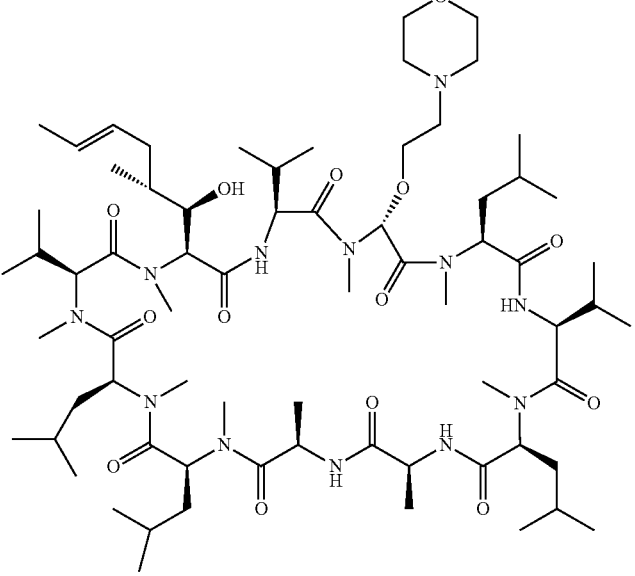 |
| 5 | 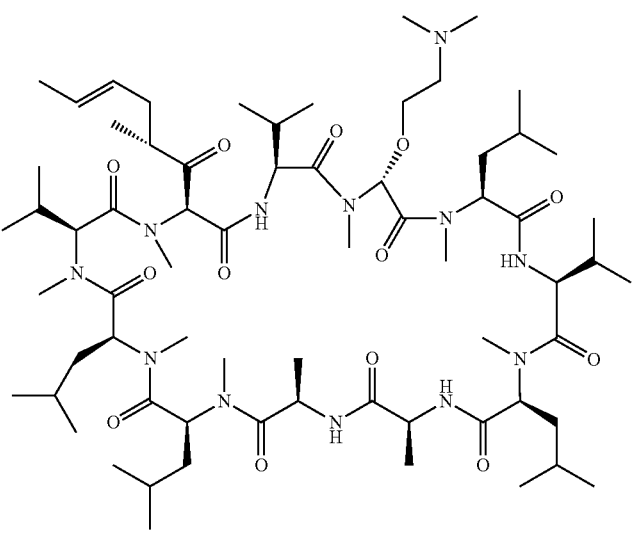 [SMILES: C/C=C/C[C@@H](C)C(=O)[C@H]1C(=O)N[C@@H](C(C)C)C(=O)N(C)[C@H](OCCN(C)C)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] |

TABLE 1-continued
| Compound No. | Compound Structure |
|---|---|
| 6 | 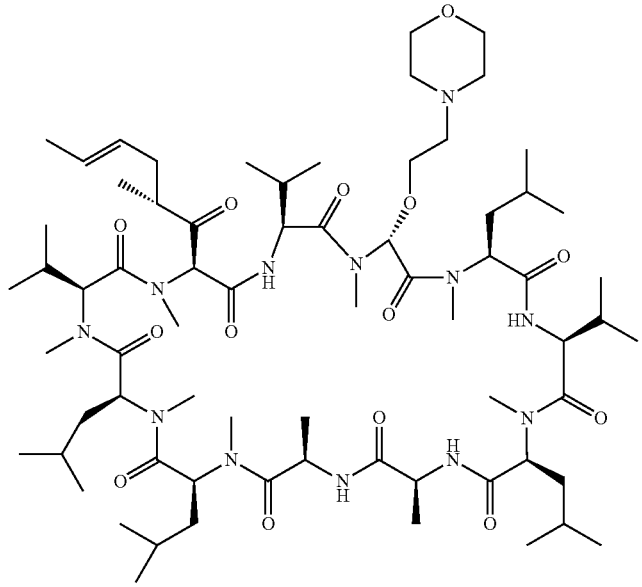 [SMILES: C/C=C/C[C@@H](C)C(=O)[C@H]1C(=O)N[C@@H](C(C)C)C(=O)N(C)[C@H](OCCN2CCOCC2)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] |
| 7 | 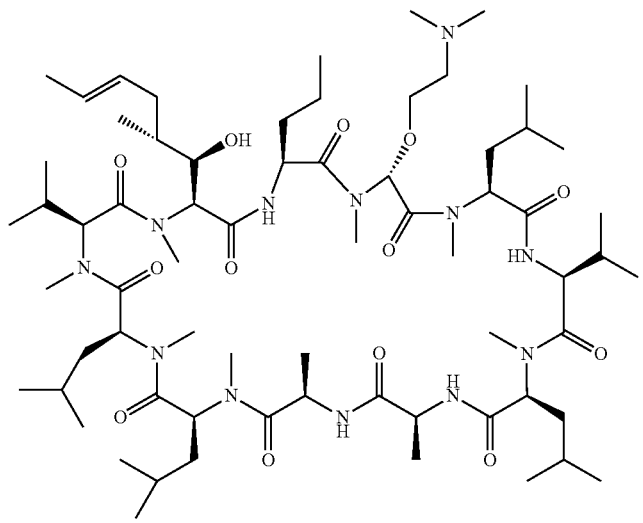 [SMILES: C/C=C/C[C@@H](C)[C@@H](O)[C@H]1C(=O)N[C@@H](CCC)C(=O)N(C)[C@H](OCCN(C)C)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] |

TABLE 1-continued
| Compound No. | Compound Structure |
|---|---|
| 8 | 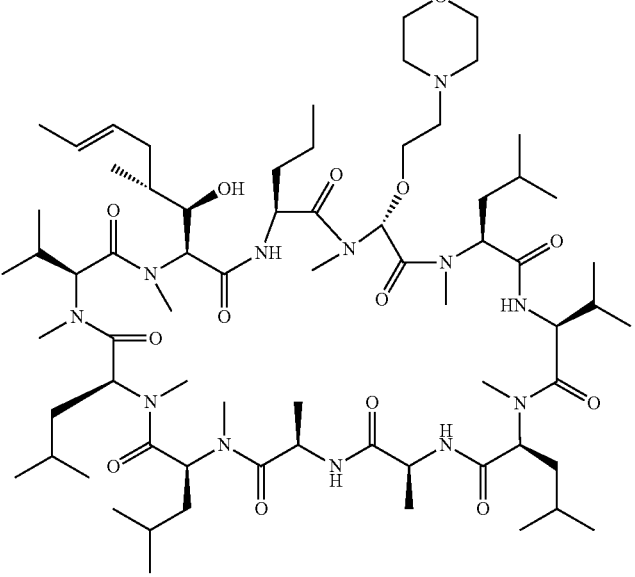 |
| 9 | 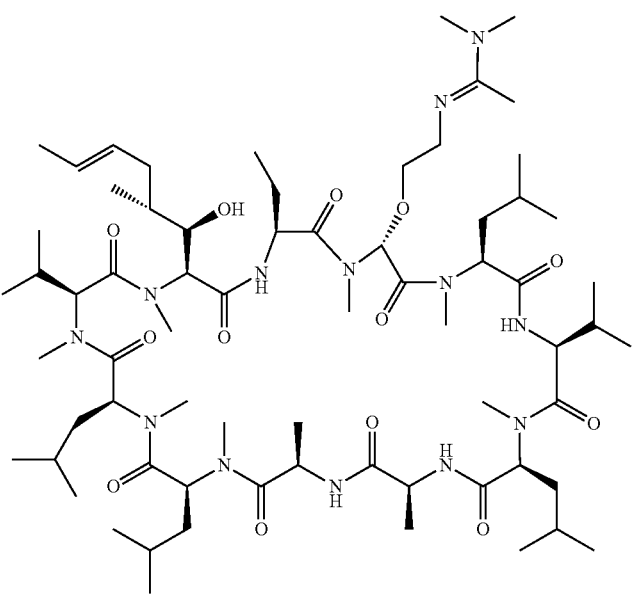 [SMILES: C/C=C/C[C@@H](C)[C@@H](O)[C@H]1C(=O)N[C@@H](CC)C(=O)N(C)[C@H](OCC/N=C(\C)N(C)C)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] |

TABLE 1-continued
| Compound No. | Compound Structure |
|---|---|
| 10 | 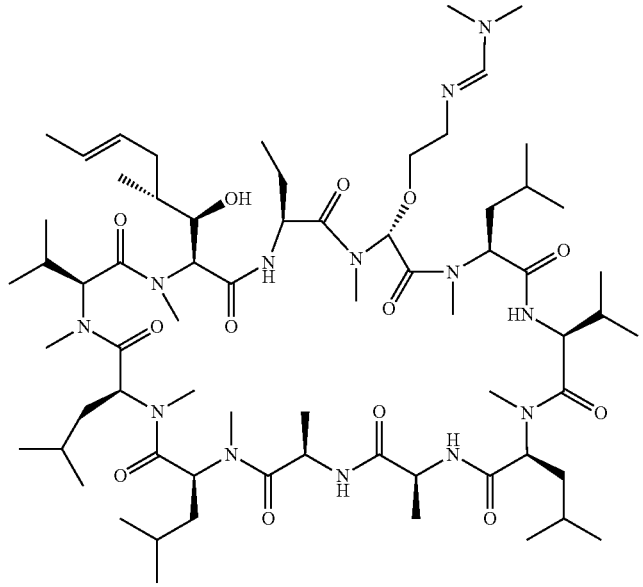 [SMILES: C/C=C/C[C@@H](C)[C@@H](O)[C@H]1C(=O)N[C@@H](CC)C(=O)N(C)[C@H](OCC/N=C/N(C)C)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] |
| 11 | 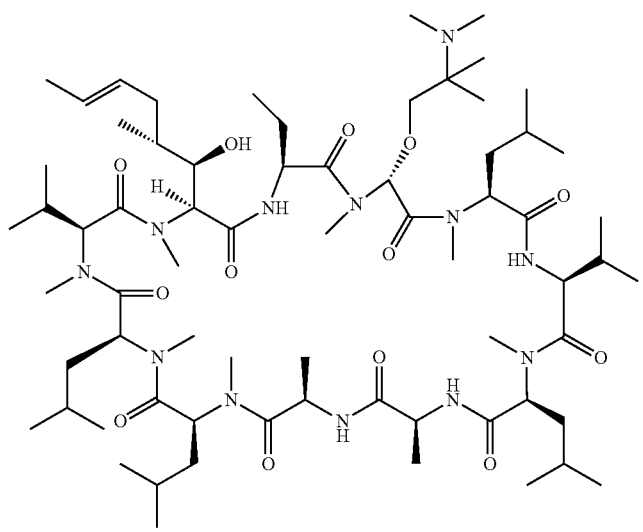 [SMILES: C/C=C/C[C@@H](C)[C@@H](O)[C@H]1C(=O)N[C@@H](CC)C(=O)N(C)[C@H](OCC(C)(C)N(C)C)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] |

TABLE 1-continued
| Compound No. | Compound Structure |
|---|---|
| 12 | 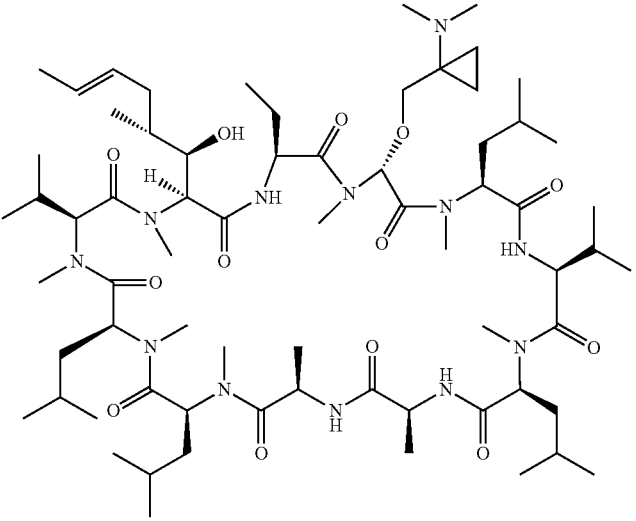 [SMILES: C/C=C/C[C@@H](C)[C@@H](O)[C@H]1C(=O)N[C@@H](CC)C(=O)N(C)[C@H](OCC2(N(C)C)CC2)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] |
| 13 | 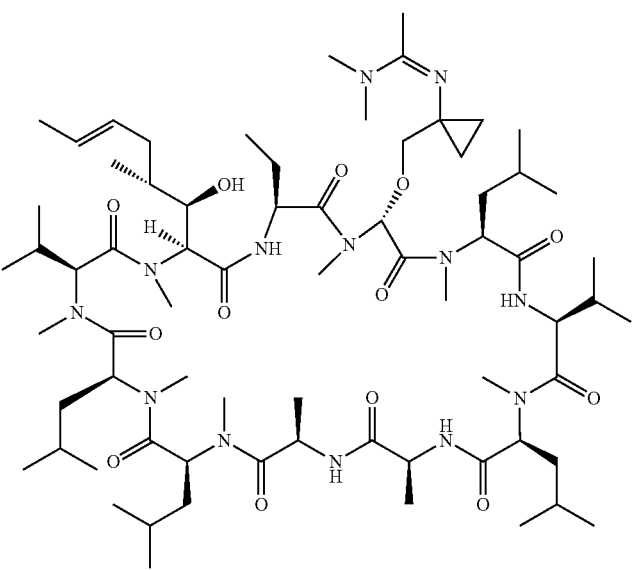 [SMILES: C/C=C/C[C@@H](C)[C@@H](O)[C@H]1C(=O)N[C@@H](CC)C(=O)N(C)[C@H](OCC2(/N=C(/C)N(C)C)CC2)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] |
| 14 | 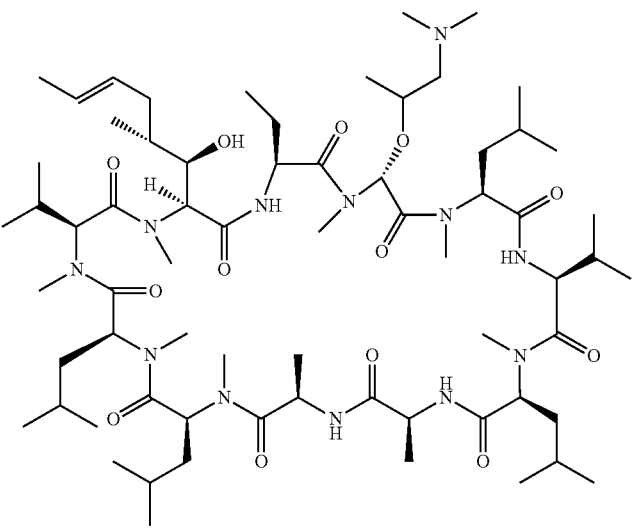 [SMILES: C/C=C/C[C@@H](C)[C@@H](O)[C@H]1C(=O)N[C@@H](CC)C(=O)N(C)[C@H](OC(C)CN(C)C)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] |

TABLE 1-continued

| Compound No. | Compound Structure |
| --- | --- |
| 15 | 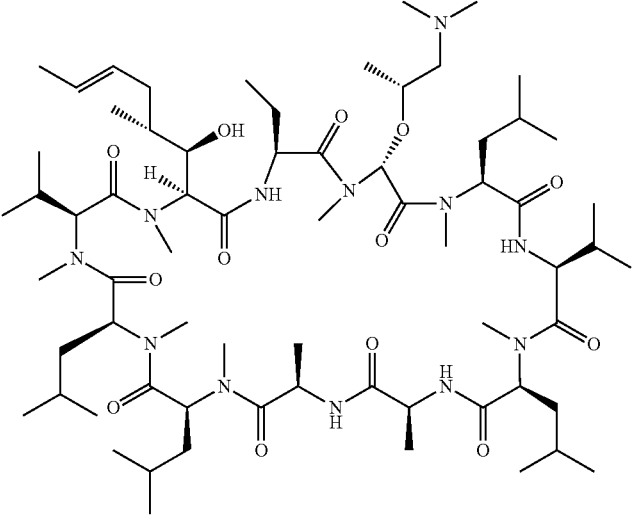 [SMILES: C/C=C/C[C@@H](C)[C@@H](O)[C@H]1C(=O)N[C@@H](CC)C(=O)N(C)[C@H](O[C@H](C)CN(C)C)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] |

In another aspect, the present disclosure may also relate to a compound of Formula 4, or a pharmaceutically acceptable salt thereof:

(Formula 4)

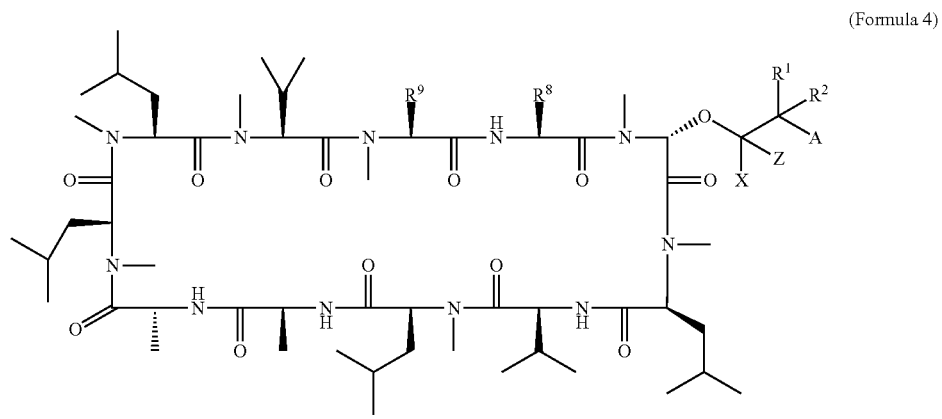

wherein X and Z are independently selected substituents, e.g. selected from H, alkyl (e.g. $C_1$-$C_6$ alkyl, for example methyl), and substituted alkyl, e.g. substituted $C_1$ to $C_6$ alkyl, or wherein X and Z are joined together to form a $C_3$ to $C_6$ cycloalkyl or heterocycloalkyl ring; and wherein A, $R^1$, $R^2$, $R^8$ and $R^9$ are as defined in any one or combination of the embodiments as described herein. Formula 4 also comprises the compounds of Formula I.

In one embodiment, X and Z are both H. In another embodiment, X and Z may be both be alkyl, e.g. methyl. In yet another embodiment, X is H and Z is methyl. Embodiments of Formula 4 may also include the following:

1.1 The compound according to Formula 4, wherein $R^1$ and $R^2$ are both hydrogen.

1.2 The compound according to 1.1 wherein at least one of $R^1$ or $R^2$ is $C_1$ to $C_6$ alkyl, e.g. methyl.

1.3 The compound according to 1.1 or 1.2, wherein $R^1$ and $R^2$ are joined together to form a $C_3$ to $C_6$ cycloalkyl or heterocycloalkyl ring, or preferably a $C_3$ to $C_6$ cycloalkyl ring, e.g. cyclopropyl.

1.4 The compound according to 1.1 to 1.3, wherein $R^8$ is ethyl.

1.5 The compound according to any one of 1.1 to 1.4, wherein $R^8$ is isopropyl.

1.6 The compound according to any one of 1.1 to 1.5, wherein $R^8$ is n-propyl.

1.7 The compound according to any one of 1.1 to 1.6, wherein $R^8$ is 1-hydroxyethyl.

1.8 The compound according to any one of 1.1 to 1.7, wherein A is —N═C($R^5$)$NR^6R^7$.

1.9 The compound according to 1.8 wherein $R^5$, $R^6$ and $R^7$ are independently selected from H, $C_1$ to $C_6$ alkyl, and optionally, substituted $C_1$ to $C_6$ alkyl.

1.10 The compound according to 1.9, wherein $R^5$ is H or $CH_3$ and wherein $R^6$ and $R^7$ are $CH_3$.

1.11 The compound according to 1.8 to 1.10, wherein $R^9$ is Formula 1a.

1.12 The compound according to any one of 1.1 to 1.11, wherein $R^9$ is Formula 1b.

1.13 The compound according to any one of 1.1 to 1.7 or 1.11 to 1.12, wherein A is $NR^3R^4$.

1.14 The compound according to item 1.13 wherein $R^3$ and $R^4$ are both —$CH_3$.

1.15 The compound according to item 1.12 to 1.14, wherein $R^3$ and $R^4$ are joined together to form a morpholinyl residue.

1.16 The compound according to 1.1 to 1.15, wherein X and Z are both H.

1.17 The compound according to 1.1 to 1.16, wherein X is alkyl (e.g. $C_1$-$C_6$ alkyl, for example methyl); and Z is H.

1.18 The compound according to 1.17, wherein $R^8$ is ethyl, and $R^9$ is Formula 1a.

In certain embodiments of Formula 4 as described herein, the provisos defined for the selection of A as described for Formula I may also apply.

In yet another aspect, the present disclosure also relates to a process for preparing the compounds according to Formula 1, 2, 3, and 4. In one embodiment, the compounds may be prepared by a method or process comprising a compound forming reaction, the reaction comprising copper triflate, and an amino alcohol. The amino alcohol may be a compound of Formula 5:

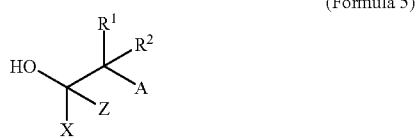

(Formula 5)

wherein the substituents, X and Z may be independently selected from H, alkyl (e.g. $C_1$-$C_6$ alkyl, for example methyl), substituted alkyl, e.g. substituted $C_1$ to $C_6$ alkyl or wherein X and Z are joined together to form a $C_3$ to $C_6$ cycloalkyl or heterocycloalkyl ring; and wherein A, $R^1$, $R^2$ are as defined in any one or combination of the embodiments as described herein. In some embodiments, the provisions defined for selection of A as described for Formula I may also apply. In one embodiment, X and Z of Formula 5 are H, with A, $R^1$, $R^2$ are as defined in any one or combination of the embodiments described herein. In another embodiment, A is $NR^3R^4$, with $R^3$ and $R^4$ defined according to any one of the embodiments or examples herein. In yet another embodiment of Formula 5, X and Z are both H; $R^1$ and $R^2$ are both H, and A is $NR^3R^4$, wherein $R^3$ and $R^4$ are both alkyl, e.g. e.g. $C_1$-$C_6$ alkyl, for example methyl).

In one embodiment, the compounds according to the present disclosure may be prepared or obtained by a process comprising reacting a cyclosporin compound (e.g. cyclosporin A, C, D, G etc) intermediate comprising a leaving group at the 3 or sarcosine position, with an amino alcohol compound, such as a compound of Formula 5. In another embodiment, the compounds as described herein may be obtainable according to a process or method comprising: a) reacting a cyclosporin compound, e.g. cyclosporin A, C, D, G, etc.) with dipyridyl disulphide to form a thiopyridyl cyclosporin intermediate (e.g. [(2'-(2-thiopyridyl)-Sar]$^3$-cyclosporin A or C, or D, or G, etc), and b) reacting said intermediate with an amino alcohol compound in the presence of copper triflate. The amino alcohols may be compounds as defined according to Formula 5 above. Examples of amino alcohol compounds which may be used include, but are not limited morpholino ethanol, or dimethylamino ethanol.

The compounds of present disclosure and invention may exist in various stereoisomeric forms and mixtures. It may be understood, that the disclosure may include, in addition to stereocenters as designated or depicted in the formulae, all their enantiomers, diastereomers, racemates or other mixtures, as well as polymorphs, solvates, hydrates, complexes, free form, or salt forms. Unless otherwise indicated, the compounds within the scope of the current disclosure comprising one or more asymmetric centers which have not been designated or depicted in the formulae, or which have not been specifically named/described may also include all enantiomers, diastereomers, or their mixtures, racemic or otherwise thereof. The representation of double bonds in the current disclosure refer to the isomer as depicted, however may be considered as also including the other Z (or E) isomer. Also included is the use of any optically pure or stereochemically pure stereoisomers, as well as any combination of stereoisomers, as determined or prepared by methods well-known in the art. Optionally, the compounds of the invention may also include their isotopes, such compounds wherein an atom is replaced with an isotope, such as hydrogen with a deuterium, or a carbon with carbon-13.

As defined herein, a pharmaceutically acceptable compound is a compound which is generally safe, non-toxic and neither biologically nor otherwise undesirable, and is acceptable and compatible for pharmaceutical use in humans. A pharmaceutically acceptable salt is a salt of a compound such as provided herein, which retains its biological properties and which is non-toxic and is compatible for pharmaceutical use.

Salts according to the present disclosure may result from the addition of acids to the compound of Formula 1, Formula 2, Formula 3, Formula 4 or any one of the specific compounds described herein. The resultant acid addition salts may include those formed with acetic, 2,2 dichloroacetic, citric, lactic, mandelic, glycolic, adipic, alginic, aryl sulfonic acids (e.g., benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g. (+)-L-tartaric), thiocyanic, undecylenic and valeric acids. In particular, acid addition salts may include those derived from mineral acids such as hydrochloric, hydrobromic, phosphoric, metaphosphoric, nitric and sulfuric acids; from organic acids, such as tartaric, acetic, citric, malic, lactic, fumaric, benzoic, glycolic, gluconic, succinic, arylsulfonic acids.

The compounds of the present disclosure may be useful for the prevention and/or treatment of diseases or medical conditions, or in the manufacture of a medicament for prevention and/or treating a disease or medical condition.

The term 'therapy' which may be used synonymously with the term 'treatment', as used herein, relates to a therapeutic intervention capable of effecting a cure, improvement, amelioration, control, control of progression, prevention of progression, prevention of reoccurrence of a disease, condition or symptom associated with said disease or condition.

As understood herein the term 'prevention', which may be used interchangeably with the term 'prophylaxis' refers to the use of a compound, or composition, for preventing the occurrence of a disease, condition or symptom, or significantly reducing the likelihood of occurrence of a disease, condition or symptom, as well as the prevention of, for example, a further reoccurrence of a disease, condition or associated symptom. Also included within the meaning of the term is the prevention of progression of a disease, condition or associated symptom, after an initial improvement or after initial removal of the cause of the disease, condition or symptom.

In particular, the compound according to the invention may be used for the prevention, as well as the treatment of cyclophilin-mediated disease or condition.

In particular, the compounds as described herein may be used as inhibitors of cyclophilin, especially cyclophilin A (CypA) and/or cyclophilin D (CypD). In one embodiment, the compound is used as an inhibitor of cyclophilin D, for example, provided or administered at a therapeutically relevant amount for the inhibition of cyclophilin D. As generally understood herein, the term 'therapeutically effective amount' is an amount of e.g. a compound which when administered to a subject (e.g. human subject) for treating and/or preventing a disease or condition, is sufficient to effect such treatment and/or prevention thereof.

The overexpression of these cyclophilins have been linked or correlated with various diseases and conditions, in particular inflammatory diseases in humans. For example, cyclophilin A has been demonstrated to function as a chemokine to facilitate leukocyte migration in support of an inflammatory response, and the blockade of cyclophilin A has been shown to be beneficial in animal models of acute inflammation. A significant body of evidence now also supports the opening of a pore at the mitochondrial membrane, termed the Mitochondrial Permeability Transition Pore (MPTP), as being critical to the onset and maintenance of a severe form of inflammation, necrotic inflammation. A key regulator of this MPTP opening is Cyclophilin D and inhibition of CypD has shown good activity in preventing tissue damage associated with necrotic inflammation. Opening of the MPTP, and subsequent initiation of necrotic cell death, is triggered by elevated intracellular calcium levels that result from a variety of factors including oxidative stress, hypoxia, bile salt toxins, etc. Pharmacological inhibition of CypD, may therefore be protective toward tissue degradation due to ischemia-reperfusion injury of organ tissue.

It has been found that compounds according to the present disclosure, as evidenced in the Examples, are surprisingly effective as inhibitors of cyclophilin, in particular cyclophilin D. The compounds may be useful for the treatment or prevention of disease or conditions, wherein raised levels or activity of cyclophilin is associated with, contributing to, or resulting in said disease or condition. In particular, the cyclophilin-mediated disease or condition which may be treated or prevented according to the invention may be a cyclophilin-D mediated disease or condition. Said disease or condition may, for example, be consequent to mitochondrial dysfunction, for example due to up-regulated opening of the MPTP.

In one embodiment, the compounds according to the present disclosure may be used as a cellular protectant (e.g. for the prevention, or reduction of cell damage or death), or as a mitochondrial protectant (e.g. for the prevention, or reduction of mitochondrial dysfunction or damage).

Cyclophilin-mediated diseases or conditions are typically diseases and conditions associated with inflammatory response, cellular damage, injury and/or cell death (e.g. necrosis) and may include, but are not limited to, the diseases and conditions as further described below.

In one embodiment, a compound according to invention may be used in the treatment and/or prevention of a disease or condition associated with cell injury, or cell death, for example cellular necrosis (unprogrammed cell death, associated with loss of cell membrane integrity and release of cellular components to extracellular matrix). The cell injury and cell death may be a consequence, or induced, for example, injury, infection, infarction, inflammation, ischemia, exposure to toxins, temperature trauma, physical trauma, etc.

As understood herein, the term 'cell' or 'cellular' may also refer to a collection or aggregate of cells, i.e. cellular tissue. Said tissue may be associated or located in a specific organ such as the kidney, liver, heart, lung, and other organs typically found in the subject to be treated.

In one embodiment, the compounds according to the invention may be used in the treatment or prevention of organ failure, or organ injury; said organ may be selected from kidney, liver, heart, lung, pancreas, intestine, cornea, skin, brain and nerve tissue. Examples of nerve tissue are for example, central, or peripheral nerve tissue. In one embodiment, the organ is a kidney. As understood herein, organ failure or organ injury may refer to the failure or injury of one, two, or multiple organs in a subject. For example, kidney failure or injury may refer to the condition of one kidney, but optionally also two, or both kidneys of a subject or patient. In one embodiment, the compounds may be used for treating and/or preventing multiple organ failure (for example, kidney, lung and liver failure).

In another embodiment, a compound according to the invention may be used for the prevention and/or treatment of a disease or condition of the kidney, i.e. a renal disease or condition. A disease or condition of the kidney may be characterized, for example by abnormal or impaired function of a kidney or a kidney tissue. Abnormal or impaired renal function may be determined according to standard clinical diagnostic methods in the art, for example but not limited to, the measurement of renal functional markers such as blood urea nitrogen and/or serum creatinine.

In a further embodiment, the compound according to the invention may be used for the prevention and/or treatment of ischemia, i.e. ischemia in a tissue or organ such as described herein. Ischemia, or ischemic injury generally occurs when the blood supply to an area of tissue or is cut-off or interrupted resulting in, amongst other factors, a lack of oxygen or an inadequate supply of oxygen to the tissue. The incidence of ischemic injury may be due to and/or be a result of, for example but not limited, to myocardial infarction, stroke, and other thrombotic events. The length of time a tissue can survive oxygen deprivation varies, but eventually ischemic tissue may become necrotic. In one embodiment, the compound may be used for the treatment of myocardial ischemia, renal ischemia, brain ischemia, or hepatic ischemia.

Ischemic injury may occur during surgery when blood vessels are cross-clamped, and in organs for transplantation. Ischemia-reperfusion (reoxygenation) injury is the tissue damage caused when the blood supply returns to the tissue after a period of ischemia or lack of oxygen (anoxia, hypoxia). Without being bound by theory, it is believed that the absence of oxygen and nutrients from the blood during the ischemic period creates a condition in which the restoration of circulation results in inflammation and oxidative damage.

In an embodiment, the compound according to the present invention may be used in the prevention, or treatment of ischemia-reperfusion injury. The ischemia-reperfusion injury may be associated with, or a consequence of a surgical procedure.

The surgical procedure may be a transplantation procedure. The ischemia-reperfusion injury may occur in recipient subjects or in donor subjects. In organ, or organ tissue transplantation, there is a period of time between removing an organ or tissue from the donor's blood supply until the reconnection of the organ or tissue to the donor recipient's blood supply. In some cases, organs may need to be transported long distances to the location of surgery, increasing the likelihood of organ damage. In one embodiment, the invention relates to use of a compound described herein for the prevention, and/or treatment of ischemia-reperfusion injury associate with, or as a consequence of an organ transplantation.

In one embodiment, the compound of the invention is administered to an organ transplant recipient (e.g. a kidney transplant recipient).

In yet a further embodiment, the ischemia-reperfusion injury is renal ischemia-reperfusion injury, which may for instance may arise from surgical procedure where blood vessels supplying a kidney are clamped for duration of at least a portion of the surgical procedure, such as kidney transplantation. In one embodiment, the compound as described herein is used for the prevention or treatment of treatment of acute kidney injury.

Kidney transplantation procedures carry risks of conditions such as acute kidney injury, which may be induced or caused by renal ischemia, and renal ischemia-reperfusion injury. Renal ischemia may result from arterial occlusion, shock and kidney transplantation, and can lead to renal cell death and kidney failure. In a further embodiment, the compound as described herein is used for the prevention or treatment of acute kidney injury associated with, or consequent to a kidney transplant procedure. For example, following removal of the donor kidney, the kidney tissue may be subject to oxygen starvation as a result of loss of blood flow (ischemia), and damage to the ischemic renal tissue may further ensue upon re-initiation of flow (reperfusion injury). The prevention of such damage, by administration of a compound which may be used as a protectant by potent inhibition of cyclophilin D and prevention of MPTP opening following ischemic stress may help improve the viability of the transplanted organ.

In other embodiments, the invention may relate to the use of a compound as described herein for the prevention or treatment of ischemia-reperfusion injury of the liver, or of the heart, optionally consequent to, or associated with transplantation of said organ or organ tissue.

According to the present disclosure, a compound or pharmaceutically acceptable salt thereof as defined herein above may be used, e.g. in the manufacture of a medicament, for preserving an organ and/or protecting an organ from organ injury, such as during transplantation surgery.

In the context of use of the compound, (e.g. in the manufacture of medicament comprising said compound) and in further in the context of transplantation surgery, the compound or medicament may be administered to an organ donor and/or to an organ recipient prior to, during, and/or after transplantation of an organ from said organ donor to said organ recipient.

In one embodiment, the compound of the invention may be administered to the donor subject prior to removal of the donor organ, for example by systemic administration e.g. injection or infusion. Alternatively, or in addition to, a compound according the present disclosure may be administered to the organ after the removal of the organ from an individual and prior to transplantation or re-attachment. For example, the compound could be added to (or included in) a fluid in which the organ is placed; and/or a compound as described herein could be added to (or included in) a fluid that is recirculated in and or through the organ.

In another embodiment, a compound according to the present disclosure may be administered to a subject, prior to commencement of surgery, for example to an organ transplant recipient prior to commencement of transplantation surgery. In yet a further embodiment, the compound may be administered during, and/or also after surgery, for example in the case of a transplant recipient during, and/or after transplantation of the organ(s) or organ tissue. In yet a further embodiment, the compound may be administered to donor (or optionally to the excised organ) and also to recipient, throughout the duration of the transplantation process and/or recovery periods. In one embodiment, the compound is administered to the transplant recipient prior to the transplantation process. In another embodiment, the compound is administered to the transplant recipient prior to, and after transplantation or an organ.

The term 'donor' or 'organ donor' as used herein refers to a subject from which the organ (or tissue of an organ) will be removed. Said donor may be a live or living donor. Alternatively, the donor may be a clinically dead donor, the term 'clinically dead' as generally understood by the skilled person and defined by standard clinical and/or legal guidelines in the art, for example as applicable to human subjects.

Furthermore, the term 'subject' or 'patient' may be used interchangeably, and refer in one embodiment, to a human subject. Preferably, the subject or patient is a human. Similarly, the term 'organ donor' or 'organ recipient' or the like as used herein may refer to a human subject. These terms may also refer to other animals, such as other mammals. The invention in further embodiments may also have application, for instance, in farm animals or other veterinary subjects, in particular mammals such cats, dogs, primates, horses, cows, and pigs. The invention may also have application in transgenic animals (e.g. transgenic pigs), where such animals have organs suitable for human transplantation.

A systemic dose of the compound of the invention can be administered to the organ donor prior to organ removal. This allows for the organ to receive a protective dose of the compound prior to removal, thereby preserving the organ by protecting the organ from damage during the removal, and up to and during the process of transplantation into the donor recipient. In the case where more than one organ is being removed from a donor, this systemic dose ensures each organ receives a dose of the compound. A systemic dose is also more likely to provide an even dose of the compound to the organ tissue that is to be transplanted. In the case where the donor is legally dead, the dose can be greater than would normally be given to a living subject.

The compound can be administered shortly before organ removal surgery, or during organ removal surgery. For example, the compound of the invention may be administered up to 8, 7, 6, 5, 4, 3, 2 or 1 hours before surgery.

In addition, or in the alternative, the organ recipient may receive a dose of the compound of the invention directly prior to receiving the organ such that their blood supply contains a protective dose of the compound of the invention, thereby preserving the transplanted organ, or body part from damage after surgery.

In the embodiments of the compound (or method or use) as mentioned herein above, the organ is any transplantable organ and can be a kidney, liver, heart, lung, pancreas, intestine, cornea, skin, brain and nerve tissue.

As described above, the present disclosure provides for administration of the compounds, acting as cyclophilin inhibitors to prevent, treat, ameliorate and/or reduce damage to organs. Optionally, the treatment may also be applied to prevention and treatment of damage to body parts such as limbs, hands, feet, fingers or toes. For example, in accidents involving severed limbs, there is a period of time between the severing of the body part from the blood supply until the reconnection of the body part to the blood supply. During this period there may also be the potential for ischaemia-reperfusion injury. In some cases, body part and patients may need to be transported long distances to the location of surgery, increasing the likelihood of damage before, during and after re-attachment. In case of body parts, these may be severed from and re-attached to the same individual, or may be given to a second individual as a transplant. There the body part is severed from a subject, the severing may be complete or partial. Partial severing may be for example severing of the blood supply but the body part remaining attached for example via skin, bone or muscle tissue. The compound may be administered (i) to a severed body part; and/or (ii) to the subject prior to re-attachment of the body part; and/or (iii) to the subject during or after re-attachment of the body part.

The compound of the present disclosure may optionally be administered together with one or more further active substances.

In a further aspect, the present disclosure provides for a compound described herein (i.e. a compound of Formulas 1, 2, 3, 4 or specific embodiments thereof) for use in the prevention or treatment of a kidney condition or disease in a subject exposed to a nephrotoxin capable of inducing said kidney condition or disease, wherein the nephrotoxin is a nephrotoxic drug substance or an endogenous nephrotoxin.

Nephrotoxins are compounds or substances which are capable of disrupting or impairing the function of a subject's kidney(s) and its associated tissues. In one embodiment of the disclosure, the nephrotoxin capable of inducing a kidney condition or disease is a nephrotoxic drug substance.

As used herein, the term 'nephrotoxic drug substance' may be an active pharmaceutical ingredient, or a pharmacologically- or diagnostically-active compound or mixture of compounds useful for medical or therapeutic applications in the prevention, diagnosis, stabilization, treatment or management of a condition, disorder or disease and which is capable of disrupting, impairing, or reducing renal function. A nephrotoxic drug substance may be provided or administered to a subject as a medicament or pharmaceutical dosage form comprising said nephrotoxic drug substance or a mixture of nephrotoxic substances, and one or more non-pharmacologically active excipients or carriers. In particular, a nephrotoxic drug substance may be a dose-limited drug substance where administration for its indicated therapeutic or diagnostic applications is restricted in terms of a threshold dose amount given at a single and/or cumulative dose due to its potential for nephrotoxic side effects. A nephrotoxic drug substance may also be further defined as a drug substance for which nephrotoxicity is listed as a side effect or as an adverse effect as per its prescribing information, and/or where its prescribed use for its intended therapeutic/diagnostic application includes an advisory for the monitoring of the dose concentration of the nephrotoxic drug substance (e.g. its serum concentration) in a subject to which it is administered, and/or the renal function of the recipient subject, for example, for signs and markers associated with nephrotoxicity.

As understood herein, the phrase 'exposure to a nephrotoxin' or similar, may refer to the exposure of a subject to a nephrotoxin during the course of a treatment for a condition, symptom or disease, wherein a subject is administered for therapeutic or diagnostic purposes, one or more doses of a nephrotoxin such as any one or combination of the nephrotoxic drug substances as defined in various embodiments herein. The phrase 'exposure to a nephrotoxin' as used herein also comprises any unintended exposure of a subject to a nephrotoxin, for example, but not limited to, accidental exposure such as from a needle-stick injury, or situational/unanticipated circumstances such as physical trauma or prolonged physical stress which may cause the release and/or build-up of endogenous nephrotoxins.

As understood herein, the term 'drug substance', as well as its genus, family, or species may refer to the drug substance as such, as well as any pharmaceutically acceptable salt, hydrate, derivative, or prodrug thereof. For example, the term 'gentamicin' may include also its common commercially available form, gentamicin sulfate. Similarly, the term 'aminoglycosides', interchangeable with the term 'aminoglycoside antibiotics' for example refers to any compound falling within its common definition or classification in the art.

In another embodiment of the disclosure, the nephrotoxin capable of inducing a kidney condition or disease is an endogenous nephrotoxin. As defined herein, an endogenous nephrotoxin is a molecule or substance (e.g. a protein) produced endogenously by a subject and is not externally administered, in contrast to the nephrotoxic drug substances described above, which may be considered as exogenous toxins. The endogenous nephrotoxin may be present in the subject or a subject's blood or blood serum at a non-nephrotoxic concentration or amount during normal physiological and homeostatic conditions, however at elevated levels i.e. above a threshold or baseline concentration may become nephrotoxic, degrade or breakdown to nephrotoxic components and/or trigger cellular or inflammatory response events leading to onset of nephrotoxicity, and kidney tissue injuries.

In one embodiment, the endogenous nephrotoxin is myoglobin, and optionally any breakdown or degradation products or released components associated with myoglobin. Myoglobin is an oxygen and iron binding protein found in muscle tissue. High levels of myoglobin and its related components may be directly toxic to kidney tubular cells, and may also lead to renal vasoconstriction, formation of intratubular casts amongst other pathologies.

Rhabdomyolysis is a condition characterized by injury or breakdown of skeletal muscle tissue, wherein their contents are released into circulation. The release of high levels of myoglobin is also associated with the related condition of myoglobinuria. Other conditions where endogenous cellular components may become nephrotoxic include, but are not limited to, conditions such as hemolysis (red blood cell lysis, where contents of damaged red blood cells e.g. heme are released into circulation), and also tumour lysis, or myeloma. Tumours in cancer patients may lyse (for example in the course of chemotherapy) and release tumour cellular content into circulation and to the kidneys.

In one embodiment, the subject to which a compound according to the present disclosure or a pharmaceutically acceptable salt thereof may be administered may have elevated serum and/or urine myoglobin levels, i.e. elevated concentration of myoglobin in blood serum and/or in urine. Alternatively, or in addition, said subject may also have any one or combination of elevated serum levels, i.e. elevated serum concentrations of: creatine phosphokinase, lactate dehydrogenase, calcium, potassium, phosphates; indicating the presence of muscle damage. In a further related embodiment, the subject to which a compound of the present disclosure, or a pharmaceutically acceptable salt thereof is provided has a serum creatine phosphokinase level of at least 5 times higher than baseline.

As defined herein, the term 'baseline' used in connection with serum concentration levels of creatine phosphokinase refers to a clinically applicable or expected serum creatine phosphokinase level or range for an individual, who for example has not yet been exposed to a nephrotoxin, or nephrotoxic levels or concentrations of an endogenous nephrotoxin e.g. myoglobin, factoring in variability which may be due to any one or combination of criteria such as, but not limited to, age-group, gender, existing co-morbidities and the like. The baseline value or baseline range for serum creatine phosphokinase, or any of the other markers may be within the knowledge of the skilled clinician or may be determined based on common methods of the art.

As defined herein, the term 'baseline' used in connection with serum levels, i.e. serum concentration of creatinine and/or blood urea nitrogen (BUN) levels, i.e. blood urea nitrogen concentration, may refer to the baseline values of these renal function markers which were determined for a subject, for example prior to commencement of exposure to a nephrotoxic drug substance (e.g. prior to a treatment regimen comprising administration of a nephrotoxic drug substance). In circumstances where the subject has not had serum creatinine or BUN levels measured prior to exposure to a nephrotoxin and prior to the onset of reduced renal functions, the term 'baseline' may refer to the clinically applicable or expected serum creatinine and/or blood urea nitrogen values, or range of values for an individual not yet exposed to the nephrotoxin, factoring variability which may be due to criteria such as, and not limited to, age-group, gender, existing co-morbidities and the like. These baseline values or range of values may be within the knowledge of the skilled clinician, and/or may be determined within common methods of the art.

A compound of Formula 1, or Formula 2 or Formula 3, or Formula 4 or a pharmaceutically acceptable salt thereof may be administered, in one embodiment, to a subject prior the subject's exposure to a nephrotoxic drug substance. Administration of a compound of Formula 1, 2 or 3, or 4 prior to exposure, as understood herein refers to administration of a first dose of said compound before a first dose of a nephrotoxic drug is administered.

Additionally, a dose of a compound according to the present disclosure, or a pharmaceutically acceptable salt thereof, in some embodiments, may be administered before any dose of the nephrotoxic drug substance is administered, such as if a nephrotoxic drug substance is administered repeatedly e.g. more than once during its prescribed course of treatment. Doses of the compound may thus be administered in a period between successive doses of the nephrotoxic drug substance. Optionally, more than one dose of a compound according to the present disclosure may be administered in a period between successive doses of a nephrotoxic drug substance.

In one embodiment, the present disclosure provides for a compound of Formula 1, 2 or 3, or 4 or a pharmaceutically acceptable salt thereof for use in the prevention or treatment of a kidney condition or disease induced by a nephrotoxic drug substance (e.g. acute kidney injury), wherein the compound or a pharmaceutically acceptable salt thereof is administered repeatedly to a subject during a first period of time which commences before and overlaps with a second period of time wherein the subject is exposed to, or is administered repeatedly the nephrotoxic drug substance. As used herein, 'repeatedly' refers to administration or exposure at least twice, i.e. more than once. The period of time may be understood as a course or period of treatment which is clinically determined for example as therapeutically relevant in regard to intended pharmacological effect in prevention, stabilization, treatment or management of the condition, disorder or disease.

In one embodiment, a compound as described herein e.g. of Formula 1, or Formula 2, or Formula 3 or 4 or a pharmaceutically acceptable salt thereof may be administered to a subject after the onset of reduced renal functions. The onset of reduced renal functions may be characterized by, amongst other physiological markers, elevated levels of serum creatinine and/or blood urea nitrogen (BUN) and/or oliguria. In one embodiment, said onset of reduced renal function may be characterized by blood urea nitrogen levels of at least 1.5 to 3 times higher than baseline and/or serum creatinine levels of at least 1.5 to 3 times higher than baseline and/or oliguria. In one embodiment, the subject has reduced renal function characterized by serum creatinine and BUN levels at least 2 times higher than baseline.

The onset of reduced renal function may in one particular embodiment be due to exposure to a nephrotoxic drug substance. For example, a subject may during the course of the treatment with a nephrotoxic drug substance suddenly develop renal impairment or dysfunction due to accumulation (e.g. blood concentration or localization to specific kidney cells or tissue) of a nephrotoxic drug substance, i.e. exposure to a cumulative dose of the nephrotoxic drug substance. Co-morbidities to the disease or condition arising or worsening during the course of treatment with a nephrotoxic drug substance may also contribute to an onset of reduced renal function, leading to acute kidney injury. In other embodiments, the onset of reduced renal function may be due to exposure to an endogenous nephrotoxin.

As used herein, the term 'dose' or 'dosage' as such refers to a single, or unit dose of a compound as described herein or a pharmaceutically acceptable salt thereof, or a drug substance, unless prefaced or followed by an indication of time, time interval or indication of quantity. A 'daily dose' or 'dosage per day' for example refers to the total dose amount of a compound as described herein, or drug substance administered in the course of one day (24 hours). A daily dose may comprise only one dose, if only one dose is administered once per day but may also be a total based on the sum of multiple unit doses that administered during a day, for example, if more than one unit dose is administered at two or more timed intervals during a day. Intervals between doses may be, for example, two doses administered approximately every 12 hours, or three doses administered approximately every 8 hours. As used herein a dose of a compound may refer to a unit dose of Compound of Formula 1, 2, 3, 4 etc., or a pharmaceutically acceptable salt thereof, but may also be applicable to a medicament, or composition or dosage form comprising said unit dose of compound or a pharmaceutically acceptable salt thereof.

In one embodiment, a dose of a compound according to the present disclosure or a pharmaceutically acceptable salt thereof may be administered to a subject within 24 hours or less before a dose of the nephrotoxic drug substance is administered to the subject. In another embodiment, the compound or a pharmaceutically acceptable salt thereof may be administered to a subject within 24 hours or less, before a dose of an aminoglycoside, e.g. gentamicin is administered to the subject.

When used herein the term 'about' or the like in connection with an attribute or value such as dose amount includes the exact attribute or precise value, as well as any attribute or value typically considered to fall within the normal or accepted variability associated with the technical field, and methods of measuring or determining said attribute or value. The term allows for any variation which in the common practice would allow for the product being evaluated to be considered bioequivalent in a mammal to the recited strength or dose of a claimed product.

It is to be understood, that the use of a compound of Formula 1, Formula 2, or Formula 3, or Formula 4, or a pharmaceutically acceptable salt thereof, or their use in a method of prevention and/or treatment of a disease or condition as described in any one of the embodiments or combination of embodiments described herein may also provide for the manufacture or preparation of a medicament or medicine adapted and prescribed for said uses or methods of treatment and/or prophylaxis.

A compound or a pharmaceutically acceptable salt thereof according to the present disclosure may be administered enterally or parenterally to a subject. In one embodiment, a compound of Formula 1, or of Formula 2, or Formula 3, or Formula 4 or a composition or a medicament comprising said compound or a pharmaceutically acceptable salt thereof may be adapted for administration or may be administered parenterally, for example by intravenous injection or by sub-cutaneous, or intramuscular injection, or by intravenous or subcutaneous infusion. In an alternative embodiment, the compound, or a composition or medicament comprising the compound may be adapted for administration, or may be administered to a subject enterally, for example orally.

The present disclosure may also relate to a medicament, or a pharmaceutical composition comprising a compound according to any one or combination of the embodiments described herein above, e.g. a compound of Formula 1, Formula 2, Formula 3, Formula 4 or a pharmaceutically acceptable salt thereof and one or more pharmaceutically acceptable excipients. The medicament or composition may comprise a therapeutically effective amount or unit dose(s) of said compound.

The medicament, or pharmaceutical composition comprising said compound may be formulated in a dosage form suitable or adapted for injection or infusion by any of the administration methods above. Alternatively, for oral administration, the medicament or pharmaceutical composition comprising a compound according to the present disclosure may be provided in a dosage form suitable or adapted for oral administration, for example such as, but not limited to a tablet, capsule, gelcap, or film. Said medicament, or pharmaceutical composition may be used in accordance with any of the methods of treatment or prevention, or uses described herein.

The following list of numbered items comprise embodiments according to the present disclosure:

1. A compound of Formula 1, or a pharmaceutically acceptable salt thereof, (Formula 1)

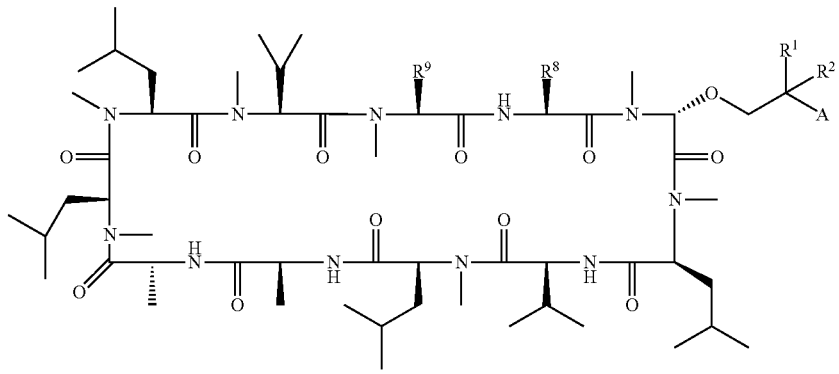

wherein:

$R^1$ and $R^2$ are independently selected from H, $C_1$ to $C_6$ alkyl, or wherein $R^1$ and $R^2$ are joined together to form a $C_3$ to $C_6$ cycloalkyl or heterocycloalkyl ring;

A is selected from:

$NR^3R^4$, wherein $R^3$ and $R^4$ are independently selected from H, $C_1$ to $C_6$ alkyl, or wherein $R^3$ and $R^4$ are joined together to form a $C_3$ to $C_6$ cycloalkyl or heterocycloalkyl ring;

and $N=C(R^5)NR^6R^7$, wherein $R^5$, $R^6$ and $R^7$ are independently selected from H, $C_1$ to $C_6$ alkyl, and optionally wherein $R^6$ and $R^7$ are joined together to form a $C_3$ to $C_6$ cycloalkyl or heterocycloalkyl ring;

$R^8$ is ethyl, 1-hydroxyethyl, isopropyl, or n-propyl;

R⁹ is Formula 1a or 1b

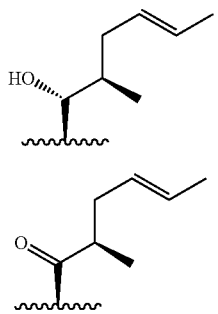

(Formula 1a)

(Formula 1b)

2. The compound according to item 1, provided that if R¹ and R² are both H and R⁸ is selected from ethyl, isopropyl, and n-propyl, R⁹ is Formula 1a and A is NR³R⁴, then R³ and R⁴ are not H, C₁-C₄ alkyl, or joined together to form an azetidinyl, pyrrolidinyl, piperidinyl, piperazinyl, morpholinyl, imidazolyl, or phthaloyl residue; or the compound according to item 1, provided that if R¹ and R² are both H, or if R¹ is methyl and R₂ is H, and R⁸ is selected from ethyl, isopropyl, and n-propyl, R⁹ is Formula 1a and A is NR³R⁴, then R³ and R⁴ are not H, C₁-C₄ alkyl, or joined together to form an azetidinyl, pyrrolidinyl, piperidinyl, piperazinyl, morpholinyl, imidazolyl, or phthaloyl residue.

3. The compound according to item 1, provided that if R¹ and R² are both H and R⁸ is selected from ethyl, isopropyl, and n-propyl, and R⁹ is Formula 1a, then A is not NR³R⁴; or the compound according to item 1, provided that if R¹ and R² are both H, or if R¹ is C₁ to C₆ alkyl and R² is H, and R⁸ is selected from ethyl, isopropyl, and n-propyl, and R⁹ is Formula 1a, then A is not NR³R⁴.

4. The compound according to item 1, provided that if R¹ and R² are both H and R⁸ is selected from ethyl, then A is not NR³R⁴; or the compound according to item 1, provided that if R¹ and R² are both H, or if R¹ is C₁ to C₆ alkyl and R₂ is H; and R⁸ is selected from ethyl, then A is not NR³R⁴.

5. The compound according to item 1 wherein R¹ and R² are both hydrogen.

6. The compound according to item 1, wherein at least one of R¹ or R² is C₁ to C₆ alkyl, e.g. methyl.

7. The compound according to item 1, wherein R¹ and R² are joined together to form a C₃ to C₆ cycloalkyl or heterocycloalkyl ring, or preferably a C₃ to C₆ cycloalkyl ring, e.g. cyclopropyl.

8. The compound according to any one of the preceding items wherein R⁸ is ethyl.

9. The compound according to any one of items 1 to 7, wherein R⁸ is selected from 1-hydroxyethyl, isopropyl, and n-propyl.

10. The compound according to any one of items 1 to 7, wherein R⁸ is n-propyl.

11. The compound according to any one of items 1 to 7, wherein R⁸ is isopropyl.

12. The compound according to any one of items 1 to 7, wherein R⁸ is 1-hydroxyethyl.

13. The compound according to any one of the preceding items, wherein R⁹ is Formula 1a.

14. The compound according to any one of the preceding items, wherein R⁹ is Formula 1b.

15. The compound according to any one of the preceding items, wherein A is NR³R⁴.

16. The compound according to item 15 wherein R³ and R⁴ are both —CH₃.

17. The compound according to item 15, wherein R³ and R⁴ are joined together to form a morpholinyl residue.

18. The compound according to any one of items 15 to 17, wherein R⁸ is 1-hydroxyethyl, isopropyl or n-propyl.

19. The compound according to any one of items 1 to 14, wherein A is —N=C(R⁵)NR⁶R⁷.

20. The compound according to item 19 wherein R⁵, R⁶ and R⁷ are independently selected from H, C₁ to C₆ alkyl and optionally, substituted C₁ to C₆ alkyl.

21. The compound according to item 20 and wherein R⁵ is H or CH₃ and wherein R⁶ and R⁷ are CH₃.

22. The compound according to items 19 to 20, wherein R⁸ is ethyl.

23. The compound according to item 1, wherein the compound, or a pharmaceutically acceptable salt thereof is of Formula 2:

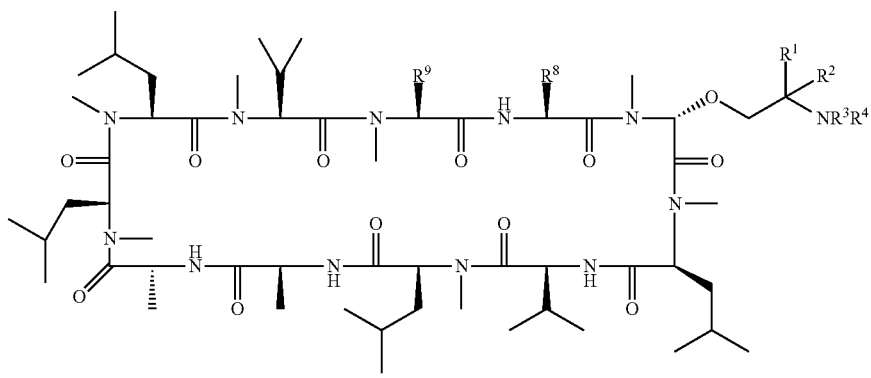

(Formula 2)

wherein:

R¹ and R² are independently selected from H, C₁ to C₆ alkyl or wherein R¹ and R² are joined together to form a C₃ to C₆ cycloalkyl or heterocycloalkyl ring;

R³ and R⁴ are independently selected from H, C₁ to C₆ alkyl, or wherein R³ and R⁴ are joined together to form a C₃ to C₆ cycloalkyl or heterocycloalkyl ring;

R⁸ 1-hydroxyethyl, isopropyl, or n-propyl; and

R⁹ is Formula 1a or 1b

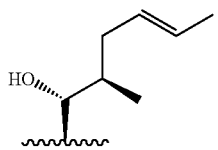
(Formula 1a)

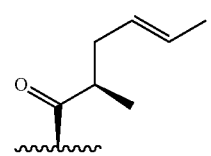
(Formula 1b)

24. The compound according to item 23 wherein $R^1$ and $R^2$ are both hydrogen.
25. The compound according to item 23, wherein at least one of $R^1$ or $R^2$ is $C_1$ to $C_6$ alkyl.
26. The compound according to item 23, wherein $R^1$ and $R^2$ are joined together to form a $C_3$ to $C_6$ cycloalkyl or heterocycloalkyl ring, or preferably a $C_3$ to $C_6$ cycloalkyl ring, e.g. cyclopropyl.
27. The compound according to any one of items 23 to 26, wherein $R^8$ is isopropyl.
28. The compound according to any one of items 23 to 26, wherein $R^8$ is n-propyl.
29. The compound according to any one of items 23 to 26, wherein $R^8$ is 1-hydroxyethyl.
30. The compound according to any one of items 23 to 29, wherein $R^3$ and $R^4$ are both —$CH_3$.
31. The compound according to any one of items 23 to 29, wherein $R^3$ and $R^4$ are joined together to form a morpholinyl residue.
32. The compound according to any one of items 23 to 31, wherein $R^9$ is Formula 1a.
33. The compound according to any one of items 23 to 31, wherein $R^9$ is Formula 1b.
34. The compound according to item 1, wherein the compound, or a pharmaceutically acceptable salt thereof is of Formula 3:

wherein:
$R^1$ and $R^2$ are independently selected from H, $C_1$ to $C_6$ alkyl or wherein $R^1$ and $R^2$ are joined together to form a $C_3$ to $C_6$ cycloalkyl or heterocycloalkyl ring;

wherein $R^5$, $R^6$ and $R^7$ are independently selected from H, $C_1$ to $C_6$ alkyl, and optionally wherein $R^6$ and $R^7$ are joined together to form a $C_3$ to $C_6$ cycloalkyl or heterocycloalkyl ring;
$R^8$ is ethyl, 1-hydroxyethyl, isopropyl, or n-propyl; and
$R^9$ is Formula 1a or 1b

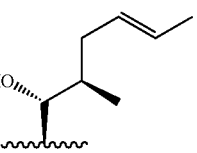
(Formula 1a)

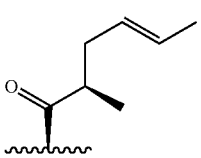
(Formula 1b)

35. The compound according to item 34 wherein $R^1$ and $R^2$ are both hydrogen.
36. The compound according to item 34, wherein at least one of $R^1$ or $R^2$ is $C_1$ to $C_6$ alkyl, e.g. methyl.
37. The compound according to item 34, wherein $R^1$ and $R^2$ are joined together to form a $C_3$ to $C_6$ cycloalkyl or heterocycloalkyl ring, or preferably a $C_3$ to $C_6$ cycloalkyl ring, e.g. cyclopropyl.
38. The compound according to any one of items 34 to 37, wherein $R^8$ is ethyl.
39. The compound according to any one of items 34 to 37, wherein $R^8$ is isopropyl.
40. The compound according to any one of items 34 to 37, wherein $R^8$ is n-propyl.
41. The compound according to any one of items 34 to 37, wherein $R^8$ is 1-hydroxyethyl.
42. The compound according to any one of items 34 to 41 wherein $R^5$, $R^6$ and $R^7$ are independently selected from H, $C_1$ to $C_6$ alkyl, and optionally, substituted $C_1$ to $C_6$ alkyl.
43. The compound according to item 42, wherein $R^5$ is H or $CH_3$ and wherein $R^6$ and $R^7$ are $CH_3$.

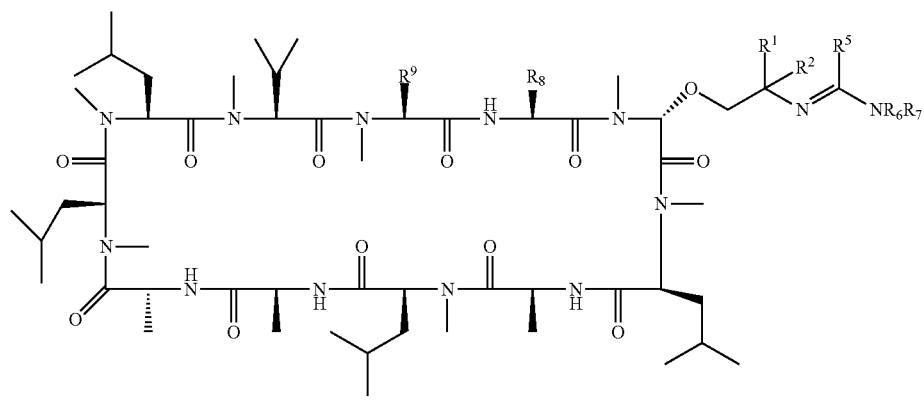
(Formula 3)

44. The compound according to any one of items 34 to 43, wherein $R^9$ is Formula 1a.
45. The compound according to any one of items 34 to 43, wherein $R^9$ is Formula 1b.

46. A compound or pharmaceutically acceptable salt thereof selected from the group of compounds as depicted in Table 1 above, or the compound according to item 1, wherein the compound, or pharmaceutically acceptable salt thereof is selected from the group consisting of compounds in Table A:

(Formula 1)

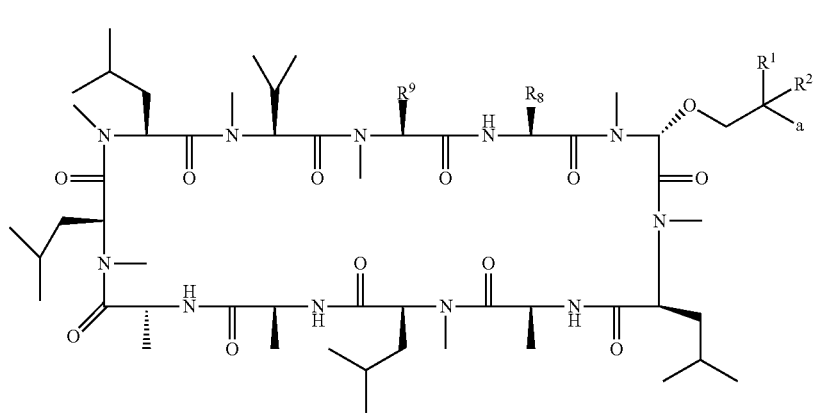

TABLE A

| Compound | $R^1$ | $R^2$ | A | $R^8$ | $R^9$ |
|---|---|---|---|---|---|
| 2 | H | H | —N(CH$_3$)$_2$ | —CH(OH)CH$_3$ | |
| 3 | H | H | —N(CH$_3$)$_2$ | —CH(CH$_3$)$_2$ | |
| 4 | H | H | morpholine | —CH(CH$_3$)$_2$ | |
| 5 | H | H | —N(CH$_3$)$_2$ | —CH(CH$_3$)$_2$ | |
| 6 | H | H | morpholine | —CH(CH$_3$)$_2$ | |
| 7 | H | H | ----N(CH$_3$)$_2$ | —CH$_2$CH$_2$CH$_3$ | |

TABLE A-continued

| Compound | R¹ | R² | A | R⁸ | R⁹ |
|---|---|---|---|---|---|
| 8 | H | H | 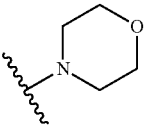 [SMILES: *N1CCOCC1] | —CH$_2$CH$_2$CH$_3$ | 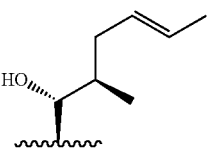 |
| 9 | H | H | —N=C(CH$_3$)N(CH$_3$)$_2$ | —CH$_2$CH$_3$ | 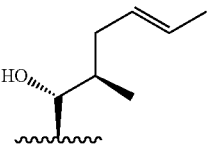 |
| 10 | H | H | —N=C(H)N(CH$_3$)$_2$ | —CH$_2$CH$_3$ | 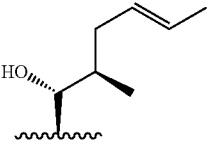 |
| 11 | CH$_3$ | CH$_3$ | —N(CH$_3$)$_2$ | —CH$_2$CH$_3$ | 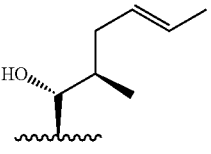 |
| 12 | —CH$_2$— | —CH$_2$— | —N(CH$_3$)$_2$ | —CH$_2$CH$_3$ | 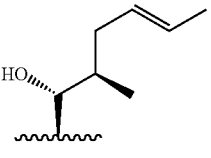 |
| 13 | —CH$_2$— | —CH$_2$— | —N=C(CH$_3$)N(CH$_3$)$_2$ | —CH$_2$CH$_3$ | 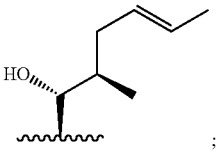 | or wherein the compound, or pharmaceutically acceptable salt thereof is selected from the group consisting of compounds 2, 5, 6, 9, 10, 11, 12, and 13 of Table A.

47. Use of a compound or a pharmaceutical acceptable salt thereof as defined in any one of items 1-46 in the manufacture of a medicament for the prevention and/or treatment of a disease or condition, e.g. a disease or condition of the kidney.

48. Use of a compound or a pharmaceutical acceptable salt thereof as defined in any one of items 1 to 46, in the manufacture of a medicament for the prevention and/or treatment of a cyclophilin-mediated disease or condition (e.g. cyclophilin A, and/or cyclophilin D); for the prevention and/or treatment of a cyclophilin-mediated disease or condition of the kidney.

49. Use of a compound or a pharmaceutically acceptable salt thereof as defined in any one of items 1 to 46, in the manufacture of a medicament for the prevention and/or treatment of a disease or condition associated with cell injury or cell death, e.g. a disease or condition of the kidney associated with cell injury or cell death.

50. The use according to item 49, wherein the disease or condition associated with cell injury or cell death is organ failure or organ injury.

51. The use according to item 50, wherein the organ is selected from the group consisting of kidney, liver, heart, lung, pancreas, intestine, cornea, skin, brain and nerve tissue.

52. The use according to any one of items 47 to 51, wherein the disease or condition is ischemia-reperfusion injury.

53. The use according to item 52, wherein the ischemia-reperfusion injury is renal ischemia-reperfusion injury.

54. The use according to any one of items 47 to 51, wherein the disease or condition is acute kidney injury.

55. The use according to item 54, wherein the acute kidney injury is associated with, or a consequence of kidney transplantation.

56. The use according to any one of items 47 to 55, wherein the medicament is administered to an organ transplant recipient.

57. The use according to any one of items 47 to 56, wherein the medicament is adapted for oral administration, or is adapted for administration by intravenous injection or infusion.

58. The use according to any one of items 47 to 57 wherein the medicament is administered to an organ donor and/or 58. to an organ recipient prior to, during, and/or after transplantation of an organ from said organ donor to said organ recipient.
59. Use of a compound or a pharmaceutically acceptable salt thereof as defined in any one of items 1 to 46 in the manufacture of a medicament for preserving an organ and/or protecting an organ from organ injury, the use comprising administering the compound to an organ donor prior to the removal of said organ from said donor, and/or to an organ recipient prior to, during or after the transplantation of said organ.
60. Use of a compound or a pharmaceutically acceptable salt thereof as defined in any one of items 1 to 46 for preserving an organ and/or protecting an organ from organ injury, the use comprising administering the compound to an organ donor prior to removal of said organ from said donor, and/or to an organ.
61. A method of preserving or protecting an organ from organ injury, wherein the method comprises a step of administering a compound or a pharmaceutically acceptable salt thereof as defined in any one of items 1 to 46 to an organ donor prior to the removal of said organ from said donor, and/or to an organ.
62. The use or method according to any one of items 59 to 61, wherein the organ is selected from the group consisting of kidney, liver, heart, lung, pancreas, intestine, cornea, skin, brain and nerve tissue.
63. The use or method according to any one of items 59 to 62, wherein the donor is a live donor, or wherein the donor is a clinically dead donor.
64. The use or method according to any one of items 59 to 64, wherein the compound is administered to the donor and/or recipient by intravenous injection or infusion.
65. The use of a compound or a pharmaceutically acceptable salt thereof as defined according to any one of items 1-46 in the manufacture of a medicament for the prevention and/or treatment of a kidney condition or disease in a subject exposed to a nephrotoxin capable of inducing said kidney condition or disease, wherein the nephrotoxin is a nephrotoxic drug substance or an endogenous nephrotoxin.
66. The use according to item 65, wherein the nephrotoxic drug substance is selected from the group consisting of antimicrobial agents, cancer chemotherapeutic agents, blood pressure medicines including ACE inhibitors and angiotensin receptor blockers, macrolactone immunosuppressive agents, HIV protease inhibitors, peptic ulcer medicines, non-steroidal anti-inflammatory drugs, proton pump inhibitors, laxatives and contrast agents.
67. The use according to item 66, wherein the nephrotoxic drug substance is a chemotherapeutic agent is selected from the group consisting of platins (e.g. carboplatin, cisplatin, oxaliplatin or nedaplatin), anthracyclines (e.g. daunorubicin, doxorubicin, idarubicin, epirubicin), bleomycins, mitomycins, actinomycins, cyclophosphamides, cytarabine, capecitabine, gemcitabine, ifosfamide, interleukin-2, streptozocin, gemtuzumab ozogamicin, melphalan, methotrexate, pemetrexed, plicamycin, and trimetrexate.
68. The use according to item 65 to 67, wherein the subject is undergoing cancer treatment, wherein said cancer treatment comprises the administration of the chemotherapeutic agent to the subject.
69. The use according to item 65 to 66, wherein the nephrotoxic drug substance is an antimicrobial agent is selected from the group consisting of, aminoglycosides (e.g. gentamicin, tobramycin, amikacin, netilmicin, apramicin, streptomycin, kanamycin, neomycin, sisomycin), beta-lactams (e.g. tazobactam, or piperacillin/tazobactam), polypeptide antibiotics (e.g. polymyxins such as polymyxin A, B, C, D, E (colistin), glycopeptide antibiotics (e.g. vancomycin), outer membrane protein targeting antibiotics, (e.g. murepavadin), antifungal agent (e.g. amphotericin B) and combinations thereof.
70. The use according to any one of items 66 or 69, wherein the subject is suffering from an infection, and wherein said infection is treated by administering the antimicrobial agent to the subject.
71. The use according to item 66, wherein the blood pressure medicine is an ACE inhibitor, optionally selected from the group consisting of captopril, benazepril, enalapril, fosinopril, and ramipril; or an angiotensin receptor blocker, optionally selected from the group consisting of candesartan, valsartan, irbesartan, olmesartan, telmisartan, eprosartan, and losartan.
72. The use according to item 66, wherein the HIV protease inhibitor is selected from the group consisting of indinavir and ritonavir.
73. The use according to item 66, wherein the peptic ulcer medicine is selected from the group consisting of cimetidine, esomeprazole, lansoprazole, omeprazole, pantoprazole, and rabeprazole.
74. The use according to item 66, wherein the non-steroidal anti-inflammatory drug is selected from the group consisting of ibuprofen, ketoprofen, diclofenac, and aspirin.
75. The use according to item 66, wherein the laxative is selected from sodium phosphate.
76. The use according to item 66, wherein the nephrotoxic drug substance is a contrast agent, optionally an iodinated contrast agent (e.g. iothalamate, or iodixanol, or iohexol).
77. The use according to item 65, wherein the endogenous nephrotoxin is myoglobin; and optionally wherein the subject has a creatine phosphokinase serum level of at least 5 times greater than baseline.
78. The use according to any one of items 77, wherein the subject has experienced or is suffering from physical trauma or crush injury, exposure to electrical current, extreme physical exertion or activity, and temperature extremes.
79. The use according to any one of items 77 or 78, wherein the medicament is administered to the subject prior to exposure to, or engagement with activities (e.g. extreme physical activity) associated with or at risk for onset of rhabdomyolysis.
80. The use according to any one of items 65 to 76, wherein the nephrotoxic drug substance is administered to the subject repeatedly; optionally wherein the nephrotoxic drug substance is administered at least twice, optionally at least once daily over a period of at least 3 days, or 7 days.
81. The use according to any one of items 65 to 80, wherein the kidney condition or disease is nephrotoxin-induced acute kidney injury or kidney failure.
82. The use according to any one of items 65 to 80, wherein the kidney condition or disease is selected from rhabdomyolysis, hemolysis, myoglobinuria, or optionally tumour lysis or myeloma-induced acute kidney injury.
83. The use according to any one of items 65 to 83, wherein the subject has a pre-existing condition or disease that increases the subject's risk of developing a kidney condition or disease when exposed to the nephrotoxin, optionally wherein said pre-existing kidney condition is chronic kidney disease; further optionally wherein the subject has a history of renal impairment or requires dialysis.

84. The use according to item 83, wherein the subject has reduced renal function, optionally wherein the subject has blood urea nitrogen levels of at least 1.5 to 3 times higher than baseline, and/or serum creatinine levels at least 1.5 to 3 times higher than baseline, and/or oliguria.

85. The use according to any one of items 65 to 84, wherein the medicament is administered to the subject prior to the subject's exposure to the nephrotoxic drug substance; optionally wherein a dose of the medicament is administered to the subject within 24 hours or less before a dose of the nephrotoxic drug substance is administered to the subject, further optionally wherein a dose of the medicament is administered to the subject within about 6 hours or less, and optionally within about 2 hours or less, before the nephrotoxic drug substance is administered to the subject.

86. The use according to any one of items 65 to 85, wherein the medicament is administered to the subject after the onset of reduced renal functions as characterized by any one or combination of: blood urea nitrogen levels of at least 1.5 to 3 times higher than baseline, serum creatinine levels of at least 1.5 to 3 times higher than baseline, and oliguria.

87. The use according to item 65 to 86, wherein a dose of the medicament is administered to the subject 1 to 24 hours after the onset of reduced renal function.

88. The use according to any one of items 65 to 87, wherein the medicament is administered repeatedly to a subject during a first period of time which commences before and overlaps with a second period of time wherein the subject is exposed to repeatedly to the nephrotoxic drug substance.

89. The use according to any one of the preceding items, wherein the recipient, donor, and/or subject is a human.

90. The use according to any one of the preceding items, wherein the medicament is adapted or formulated for administration by infusion or by injection, preferably subcutaneous, intramuscular or intravenous injection or intravenous or subcutaneous infusion; or is adapted or formulated for oral administration.

91. A compound or a pharmaceutically acceptable salt thereof as defined in any one of items 1 to 46, for use as a medicine.

92. A compound or a pharmaceutically acceptable salt thereof as defined in any one of items 1 to 46, for use in the prevention and/or treatment of a disease or condition, e.g. of the kidney or an organ or tissue thereof.

93. A compound for use as defined in item 91 as a cyclophilin inhibitor (e.g. cyclophilin A and/or cyclophilin D inhibitor); preferably for use in the prevention or treatment of a cyclophilin-mediated disease or condition, e.g. a cyclophilin (e.g. cyclophilin A and/or D)-mediated disease or condition of the kidney.

94. A compound for use according to items 91 to 93, wherein the use comprises any one or combination of the features as described in items 50 to 58.

95. A compound or a pharmaceutically acceptable salt thereof as defined in any one of items 1-46 for use in the preservation of an organ and/or protecting an organ from organ injury, the use comprising administering the compound to an organ donor prior to the removal of said organ from said donor and/or to an organ recipient prior to, during or after the transplantation of said organ.

96. The compound for use according to item 95, wherein the use comprises any one or combination of features as described in 62 to 64.

97. A compound or a pharmaceutically acceptable salt thereof as defined according to any one of items 1-46 for use in the prevention and/or treatment of a kidney condition or disease in a subject exposed to a nephrotoxin capable of inducing said kidney condition or disease, wherein the nephrotoxin is a nephrotoxic drug substance or an endogenous nephrotoxin.

98. The compound for use according to item 97, further comprising any one or any combination of the features as defined in items 66 to 90.

99. The compound for use according to any one of items 91 to 98, wherein compound or medicine is administered to a human subject, donor, or recipient.

100. A method for prevention and/or treating a disease or condition comprising administering a compound or a pharmaceutically acceptable salt thereof as defined in any one of items 1 to 46, to a subject in need thereof; preferably wherein the subject is a human subject.

101. The method according to item 100, wherein the disease or condition is a disease or condition of the kidney.

102. A method of inhibiting cyclophilin or for preventing and/or treating a cyclophilin-mediated disease or condition by the inhibition of cyclophilin, comprising administering a compound or a pharmaceutically acceptable salt thereof as defined in any one of items 1 to 46 to a (human) subject in need thereof, optionally wherein the cyclophilin is cyclophilin A or cyclophilin D; further optionally wherein the cyclophilin-mediated disease or condition is a kidney disease or condition.

103. The method according to item 100 to 101, wherein the method comprises any one or combination of features as defined in 50 to 58.

104. A method for preserving an organ and/or protecting an organ from organ injury, comprising administering a compound or a pharmaceutically acceptable salt thereof as defined in any one of items 1-46 to an organ donor prior to the removal of said organ from said donor and/or to an organ recipient prior to, during or after the transplantation of said organ.

105. The method according to item 104, wherein the method comprises any one or combination of features as defined in items 62 to 64.

106. A method for preventing and/or treating a kidney condition or disease in a subject exposed to a nephrotoxin capable of inducing said kidney condition or disease, wherein the nephrotoxin is a nephrotoxic drug substance or an endogenous nephrotoxin and wherein the method comprises administering to said subject a compound according any one of items 1-46, or a pharmaceutically acceptable salt thereof.

107. The method according to item 106, wherein the method comprises any one or combination of the features as defined in items 60 to 90.

108. A pharmaceutical composition comprising a compound or a pharmaceutically acceptable salt thereof as defined in any one of items 1 to 46, and one or more pharmaceutically acceptable excipients.

109. A compound of Formula 4, or a pharmaceutically acceptable salt thereof,

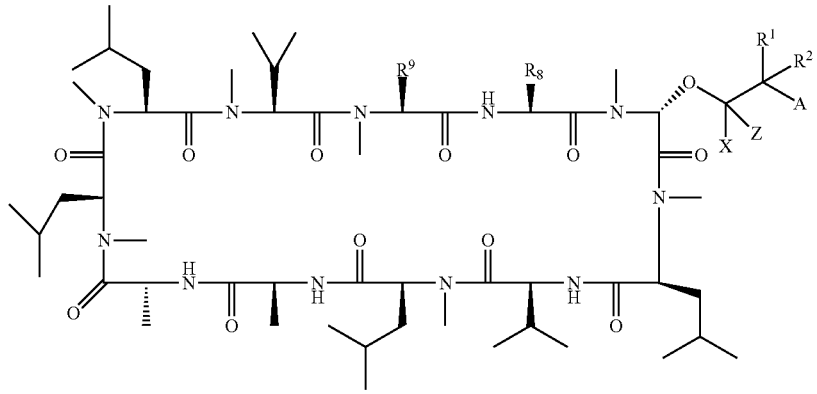

(Formula 4)

wherein X and Z are independently selected substituents, e.g. selected from H, alkyl (e.g. $C_1$-$C_6$ alkyl, for example, methyl), and substituted alkyl (e.g. substituted $C_1$ to $C_6$ alkyl), or wherein X and Z are joined together to form a $C_3$ to $C_6$ cycloalkyl or heterocycloalkyl ring; and wherein A, $R^1$, $R^2$, $R^8$ and $R^9$ are as defined in any one of the features or combinations described in items 1 to 22.

110. The compound of item 109, wherein X and Z are both H, or wherein X and Z are both alkyl, e.g. methyl; or wherein one of X or Z is alkyl, e.g. $C_1$-$C_6$ alkyl (for example, methyl).

111. The compound of item 109 or 110, wherein A is $NR^3R^4$, e.g. wherein $R^3$ and $R^4$ are both alkyl, e.g. $C_1$-$C_6$ alkyl, e.g. methyl.

112. Use of a compound according any one of items 109 to 111 for the manufacture of a medicament according to any one or combination of features as defined in items 47 to 90.

113. A process for the preparation of any one of the compounds of Formula 1, 2, 3 or 4 as defined in items 1 to 46, or 109 to 111, the process comprising a step of reacting a cyclosporin intermediate (e.g. an intermediate of cyclosporin A, C, D, G, etc., e.g. a thiopyridyl intermediate, with an amino alcohol compound, and optionally, copper triflate.

114. The process of item 113, wherein the amino alcohol is a compound of Formula 5:

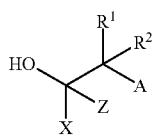

(Formula 5)

wherein X and Z are independently selected from H, alkyl (e.g. $C_1$-$C_6$ alkyl, for example methyl), substituted alkyl (e.g. substituted $C_1$ to $C_6$ alkyl); or wherein X and Z are joined together to form a $C_3$ to $C_6$ cycloalkyl or heterocycloalkyl ring; or wherein X and Z are as described in items 110 to 111; and wherein A, $R^1$, and $R^2$ are as defined according to any one of the features or combinations thereof as described in items 1 to 22.

The following examples serve to illustrate the invention, however should not to be understood as restricting the scope of the invention.

EXAMPLES

Example 1—Compound Preparation

The compounds as described herein may be obtainable in accordance to the general synthesis route as depicted below, comprising: a first step of reacting a cyclosporin compound (for example, cyclosporin A, C, D, G, etc) with dipyridyl disulphide to form a thiopyridyl intermediate ([(2'-(2-thiopyridyl)-Sar]$^3$-cyclosporin A or C, or D, or G, etc), such as a compound of formula I as depicted below, followed by a second step comprising the reaction of this intermediate with an amino alcohol compound in the presence of copper triflate. Examples of amino alcohol compound used include, but are not limited to, amino ethanol compounds such as morpholino ethanol, or dimethylamino ethanol.

The skilled person will appreciate, that different analogues may be prepared using different amino alcohol reagents in the second step, for example, where the N-amino substituents on the amino alcohol could also be changed to give further analogues (examples of N-amino substituents include, and are not limited to: methyl, ethyl, propyl, isopropyl, n-butyl, sec-butyl, tert-butyl).

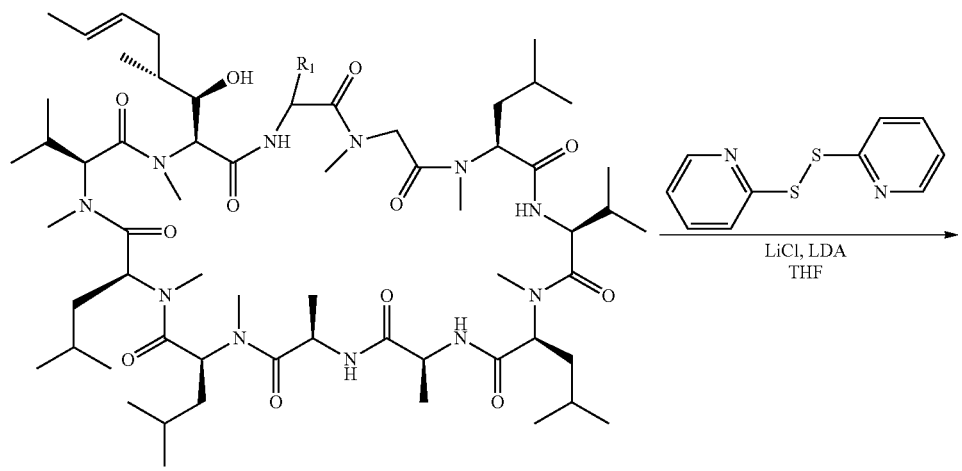
Cyclosporin C: R₁ = 1-hydroxyethyl
Cyclosporin D: R₁ = isopropyl
Cyclosporin G: R₁ = n-propyl
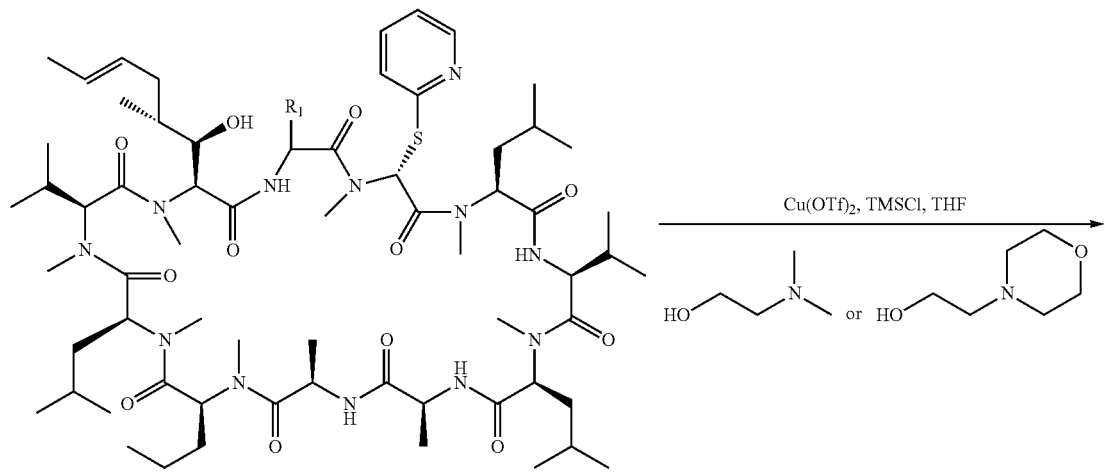
I
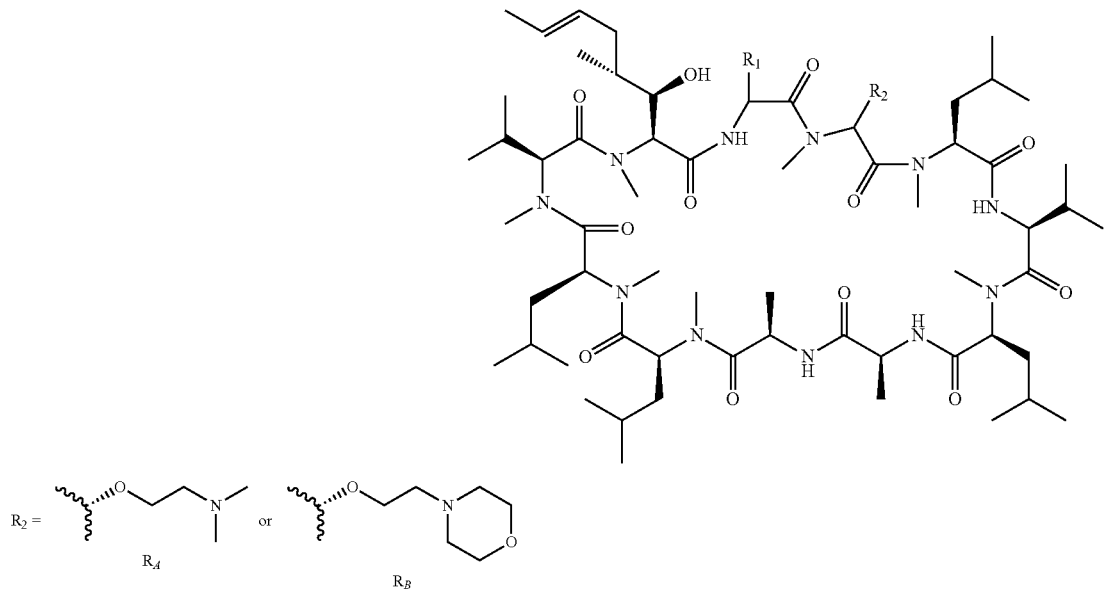

The following procedure described for the preparation of compound 2 (ref. Table 1, Table A above) may be applied as a general procedure for preparing compounds with analogous substitution at the 3-position of a cyclosporin:

Preparation of Compound 2

Step I: A solution of cyclosporin C (100 mg, 0.082 mmol) in 1.5 mL THF was added into a three-necked-flask. Then 106 mg of LiCl was added. The mixture was cooled down to 0° C. under $N_2$. A LDA solution (2M solution in THF, 1.6 mmol) was added dropwise to the mixture. The mixture was stirred at 0° C. for 1 hour. A solution of dipyridyl disulfide (55 mg, 0.25 mmol) in 0.5 mL THF was added dropwise to the mixture. The mixture was stirred at 0° C. for 1 hour. Thereafter, 1 mL MeOH was added to the mixture. Then the mixture was allowed to be stirred for another 16 hours at −5° C.

The mixture was quenched with 5 mL of a $NaH_2PO_4$ saturated solution, and then extracted three times with each 5 mL of MBTE. The organic phase was dried with $Na_2SO_4$ and concentrated to obtain 200 mg crude product. The thiopyridyl intermediate was obtained by purification using column chromatography.

Step II: $Cu(OTf)_2$ (40.0 mg, 0.11 mmol) and 4A molecular sieves (40 mg) was added into a reaction flask containing 1.0 mL of THF. The mixture was stirred at 40° C. for 1 hour under $N_2$. After removing the solvent on vacuum, a solution of intermediate 1a (20.0 mg, 0.015 mmol) in 0.5 mL THF was added to the residue. The mixture was stirred at room temperature for 1 hour. Dimethylamino ethanol (12.6 mg, 0.14) was added dropwise to the mixture, followed by TMSCl (20.0 mg, 0.18 mmol). The resulting mixture was stirred at 30° C. for 16 hours. The mixture was then quenched with 5 mL water, extracted with iPrOAc. The organic phase was dried with sodium sulfate and concentrated. The crude product chromatographed to give the desired product compound 2 (($^1$H-NMR (400 MHz $CDCl_3$, δ (ppm)): 6.18, sarcosine residue); HRMS Electrospray (M+1) 1306.10; 1307.10); mass according to isotope distribution: 1304.90 (100%); 1305.91 (71.4%)).

Reaction of thiopyridyl intermediate obtained in Step I with morpholino ethanol instead of dimethylamino ethanol provided the corresponding derivative compound 2b:

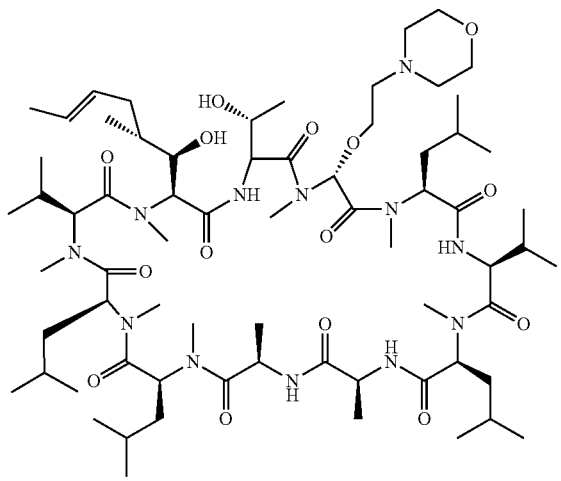

2b

Preparation of Compounds 3, 4, 7 and 8

Cyclosporin derivatives based on cyclosporin D, and cyclosporin G may be prepared using an analogous method as described for preparation of compound 2; in a first step to provide a thiopyridyl intermediate, followed by a second step of reaction with respective ethanol derivatives (e.g. morpholino ethanol, or dimethylamino ethanol) to provide, following chromatographic purification, compound 3 (($^1$H-NMR (400 MHz $CDCl_3$, δ (ppm)): 5.96, sarcosine residue); HRMS Electrospray (M+1) 1304.15; 1305.10; mass according to isotope distribution 1302.93(100%) 1303.93 (72.5%)), compound 4 (($^1$H-NMR (400 MHz $CDCl_3$, δ (ppm)): 6.01, sarcosine residue); HRMS Electrospray (M+1) 1346.25; 1347.45; mass according to isotope distribution 1344.94 (100%), 1345.94 (74.6%)), compound 7 (($^1$H-NMR (400 MHz $CDCl_3$, δ (ppm)): 5.76, sarcosine residue); HRMS Electrospray (M+1) 1304.10; 1305.15; mass according to isotope distribution 1302.93(100%), 1303.93 (72.5%)) and compound 8 (($^1$H-NMR (400 MHz $CDCl_3$, δ (ppm)): 5.80, sarcosine residue); HRMS Electrospray (M+1) 1346.25; 1346.75; mass according to isotope distribution 1344.94 (100%), 1345.94 (74.6%)).

Preparation of Compound 5 and Compound 6

A solution of compound 3 (6.0 mg, 0.0046 mmol) in 2.4 mL DMSO was added into a 10 mL reaction vessel, followed by 2-iodooxbenzoic acid (Dess-Martin reagent, 120.0 mg, 0.43 mmol) was added to the solution. The mixture was stirred at room temperature for 24 hours. The mixture was then quenched with 12 mL of water, extracted with iPrOAc. The organic phase was dried and concentrated. The crude was purified by chromatography to give 3.0 mg of the desired product, compound 5 (($^1$H-NMR (400 MHz $CDCl_3$, δ (ppm)): 5.98, sarcosine residue); HRMS Electrospray (M+1) 1302.30; 1303.60; mass according to isotope distribution 1300.91(100%), 1301.91 (72.5%)).

Analogously, compound 4 may be oxidized under similar reaction conditions with the Dess-Martin reagent to provide compound 6 (($^1$H-NMR (400 MHz $CDCl_3$, δ (ppm)): 6.01, sarcosine residue); HRMS Electrospray (M+1) 1344.30; 1345.00; mass according to isotope distribution 1342.92 (100%), 1343.92 (74.6%)).

Preparation of Compound 9 and Compound 10

Compounds 9 and 10 were prepared from intermediate II (2'-(2-aminoethoxy)-Sar]3-cyclosporin A), which may be prepared according to the methods described in WO2019/016572.

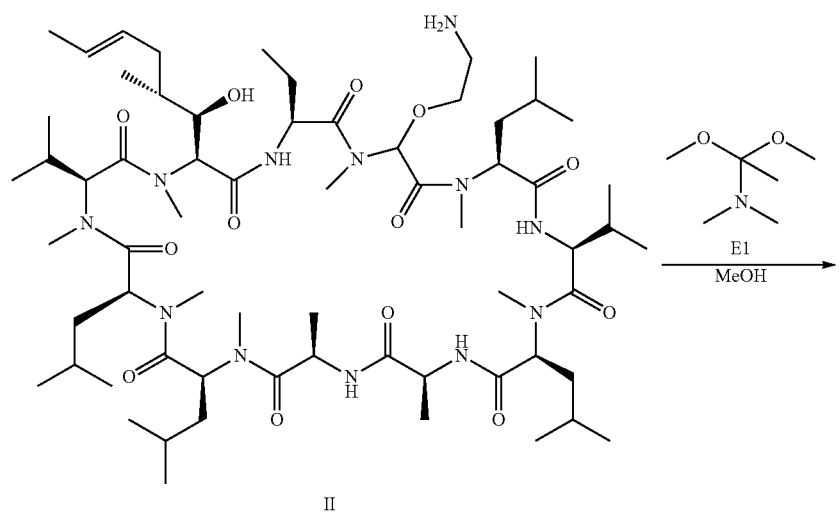

II

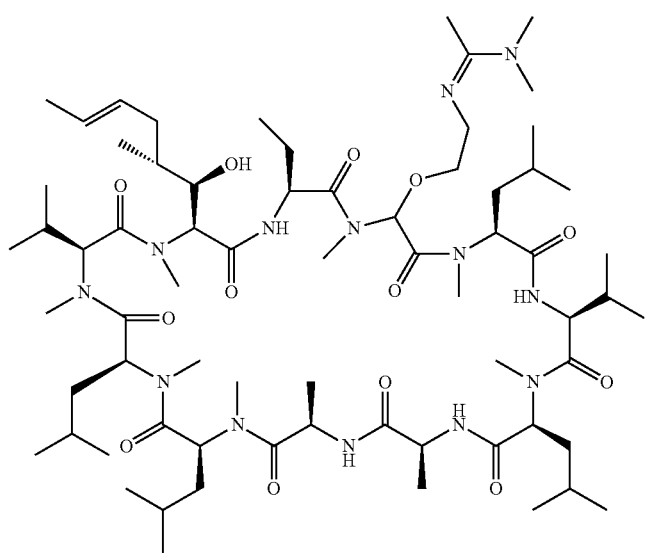

9

Compound II (10.0 mg, 0.0079 mmol) was dissolved in 5 mL of MeOH under N₂. Dimethylacetamide, dimethyl acetal (E1 3.2 mg, 0.024 mmol) was added to the solution. The mixture was stirred at 70° C. for 2 hours. The mixture was concentrated to dryness and the desired compound 9 was obtained by chromatography. (($^1$H-NMR (400 MHz CDCl₃, δ (ppm)): 5.90, sarcosine residue); HRMS Electrospray (M+1) 1331.15; 1332.30; mass according to isotope distribution 1329.94 (100%); 1330.94 (73.5%)).

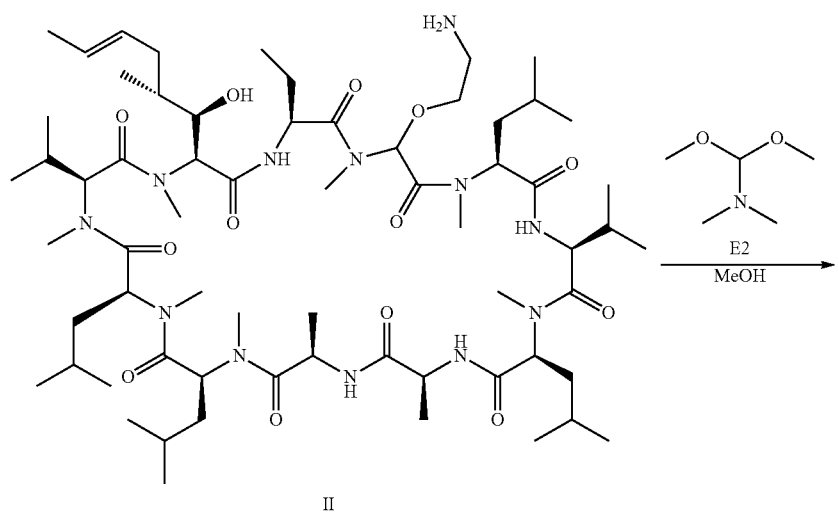

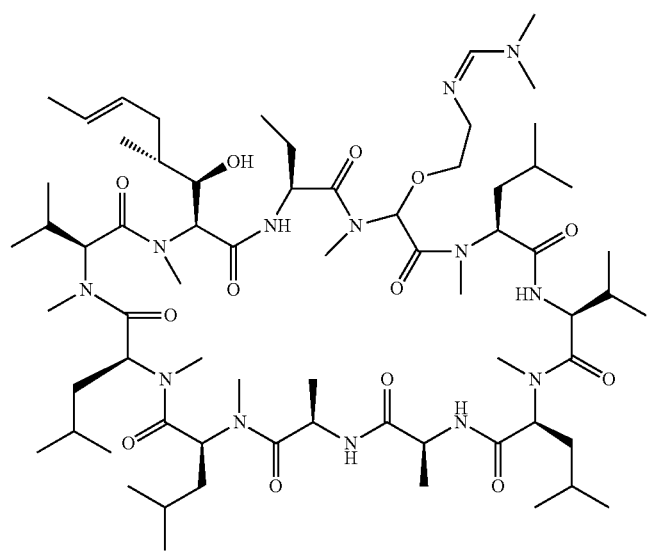

Compound 10 was prepared analogously by reaction of compound II with dimethylformamide dimethyl acetal (E2). Compound 10 (($^1$H-NMR (400 MHz CDCl$_3$, δ (ppm)): 5.91, sarcosine residue); HRMS Electrospray (M+1) 1317.15; 1318.05; mass according to isotope distribution 1315.92 (100%), 1316.92 (72.5%)).

Preparation of Compounds 11 and 12

Compounds 11 and 12 were prepared from intermediate III (2'-(2-thiopyridyl)-Sar]$^3$ cyclosporine A), the preparation of which is also described in WO2019/016572.

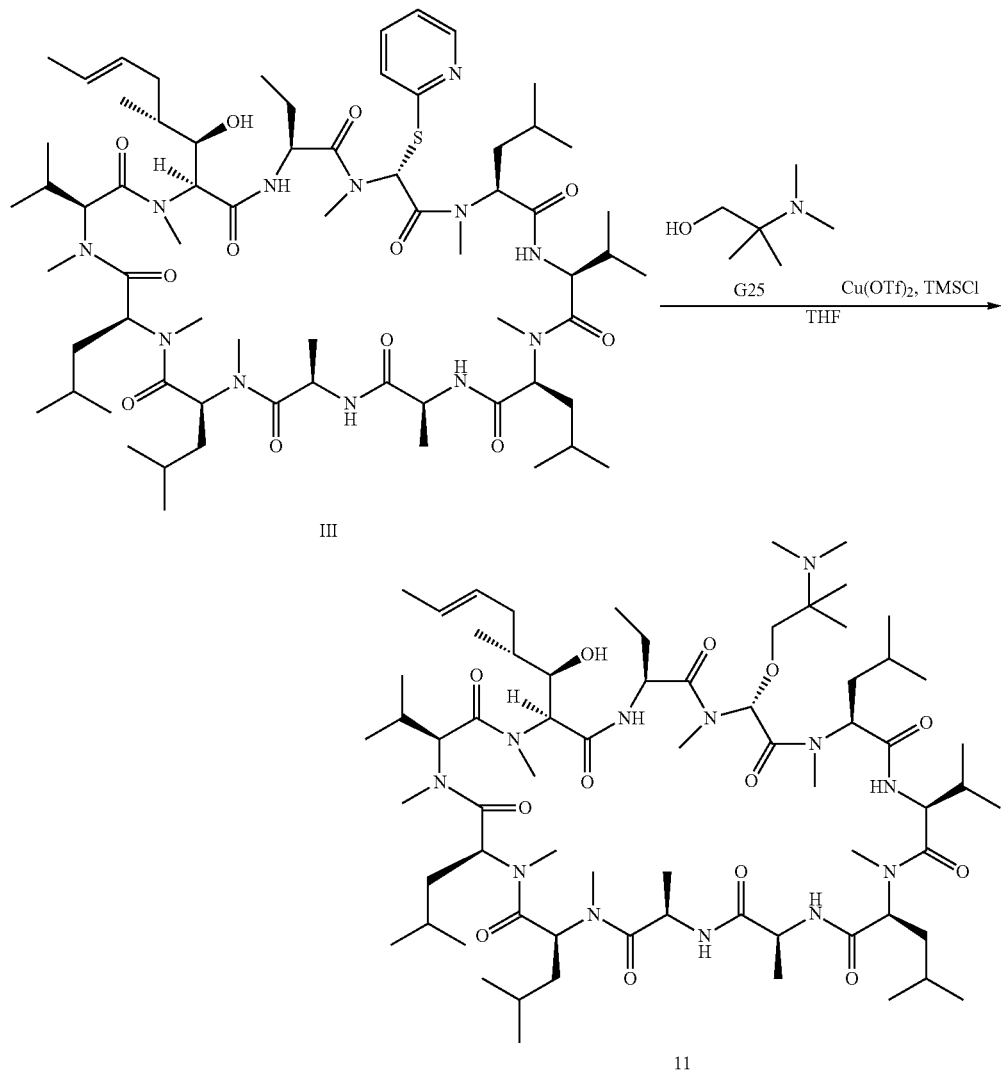

The Cu(OTf)$_2$ catalyst (5.0 g, 16.39 mmol) was placed in 15 mL THF and cooled down to 0° C. A solution of III (5.0 g, 3.81 mmol) and G25 (1.9 g, 16.39 mmol) in 35 mL TH was added to the flask. TMSCl (1.0 g, 9.15 mmol) was finally added dropwise to the mixture. The mixture was then stirred at 20-25° C. After 16 hours, the reaction mixture was poured into 150 mL of water. Aqueous K$_2$CO$_3$ was added to adjust the pH to 10. i-PrOAc (50 ml) was added to the mixture and insoluble were filtered off. The filtrate was extracted with i-PrOAc(50 mL*2). The organic phase was washed twice with aqueous solution of malic acid. The aqueous phase was combined and adjusted the pH value to 8, and extracted again with i-PrOAc. The organic phase was washed with brine, dried over magnesium sulfate, and concentrated to give 1.4 g of compound 11. The product was further purified via chromatography. Compound 11 (($^1$H-NMR (400 MHz CDCl$_3$, δ (ppm)): 5.90, sarcosine residue); HRMS Electrospray (M+1) 1317.80; 1318.70; mass according to isotope distribution 1316.94 (100%), 1317.94 (73.5%)).

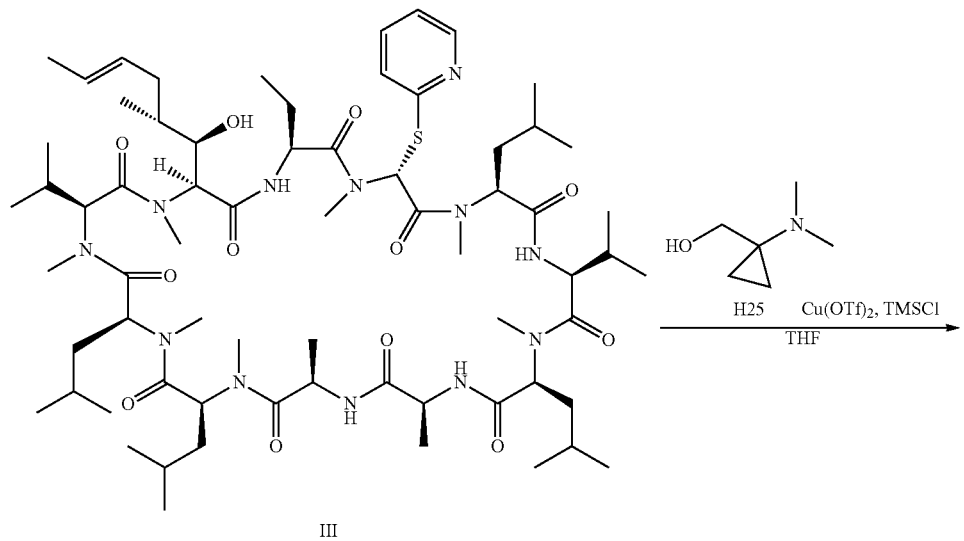
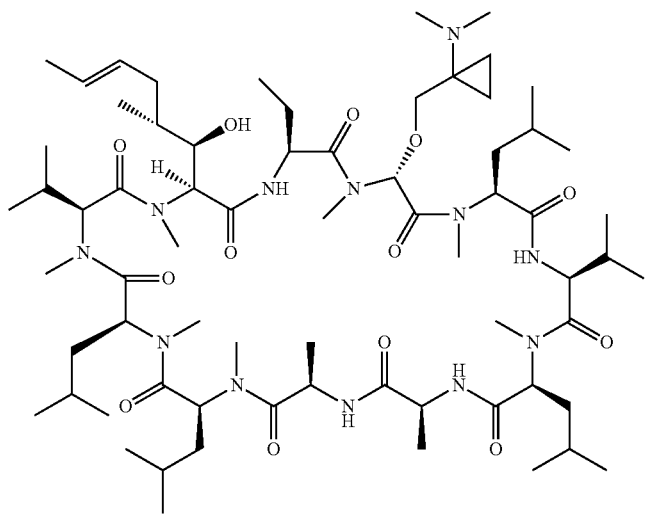
Compound 12 was prepared under analogous conditions by reaction of III with H25 Compound 12 (($^1$H-NMR (400 MHz CDCl$_3$, δ (ppm)): 5.82, sarcosine residue); HRMS Electrospray (M+1) 1315.70; 1316.60; mass according to isotope distribution: 1314.93 (100%), 1315.93 (73.5%)).

Preparation of Compound 13

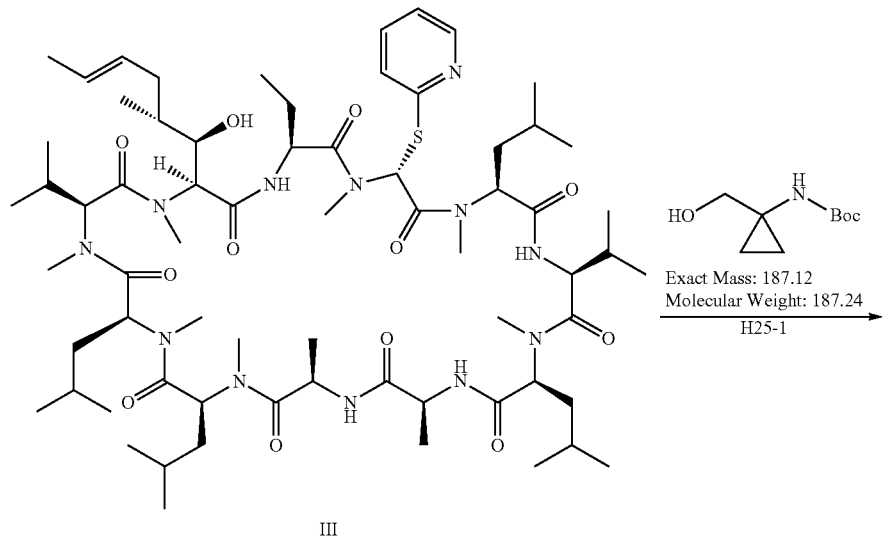

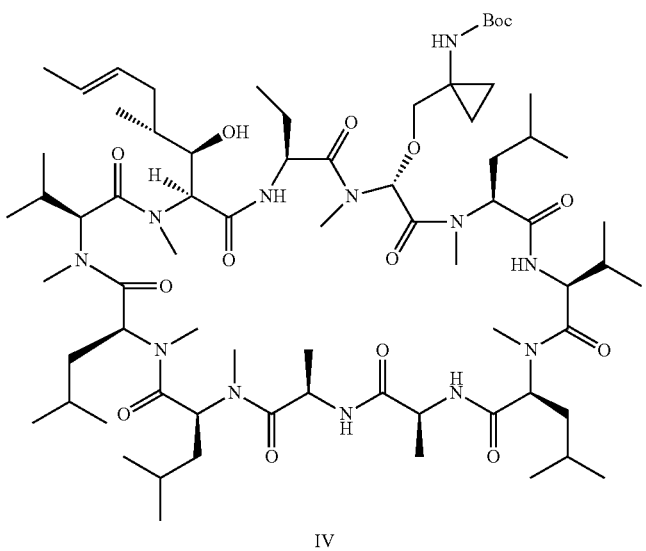

Step 1: To a stirred solution of III (5 g) and H25-1 (3.1 g) in 50 mL of THF, at 0° C. under N₂, was added firstly Cu(OTf)₂ (5 g), followed by TMSCl (99 mg). The resulting mixture was stirred for 16 hours at RT under N₂. The resulting mixture was poured into 50 mL water, and then 50 mL i-PrOAc was added. The aqueous phase was adjusted to pH 8.0 by the addition of aqueous K₂CO₃. The aqueous phase was separated and was extracted by another portion of i-PrOAc. The combined organic phase was washed twice with aqueous malic acid (2.1 g malic acid in 50 mL water). After separation of the phases, the pH of the aqueous phase was adjusted to 8.0 pH with the addition of aqueous K₂CO₃. The aqueous solution was then extracted by twice 50 mL i-PrOAc. The organic phase was dried and concentrated to obtain 4.7 g crude IV, which was used directly in the next step.

Step 2: Compound IV (4.7 g) obtained from step 1 was dissolved in 25 mL DCM. TFA (25 mL) was added under N₂ at 0° C. The mixture was stirred at RT for 2 hours. The mixture was then concentrated under vacuum. The residue was dissolved in 50 mL EtOAc and was washed twice with 50 mL saturated NaHCO₃. The organic phase was dried and concentrated to give 3.9 g crude intermediate V. The crude product was purified by chromatography to yield 1.7 g of compound V $^{1}$H-NMR (400 MHz CDCl₃, δ (ppm)): 6.02, sarcosine residue; observed HRMS (Electrospray M+1): 1287.8/1289.0; calculated mass according to isotope distribution: 1286.89 (100%), 1287.9 (71.4%)).

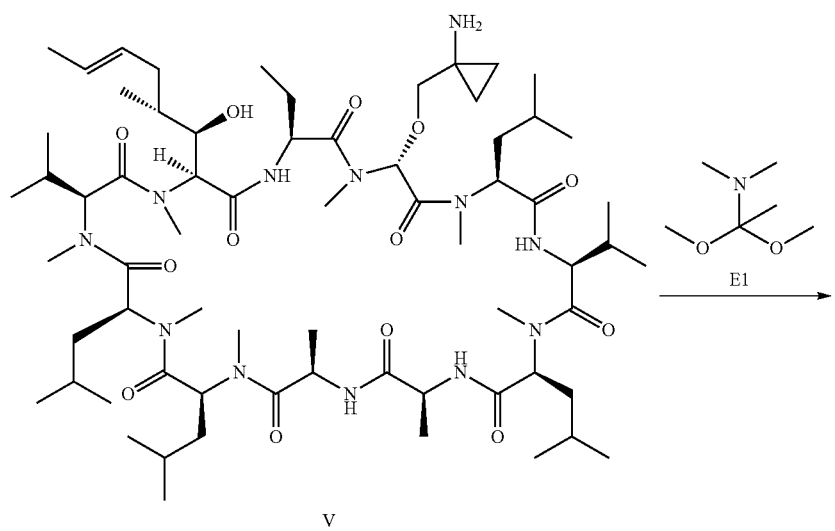

V

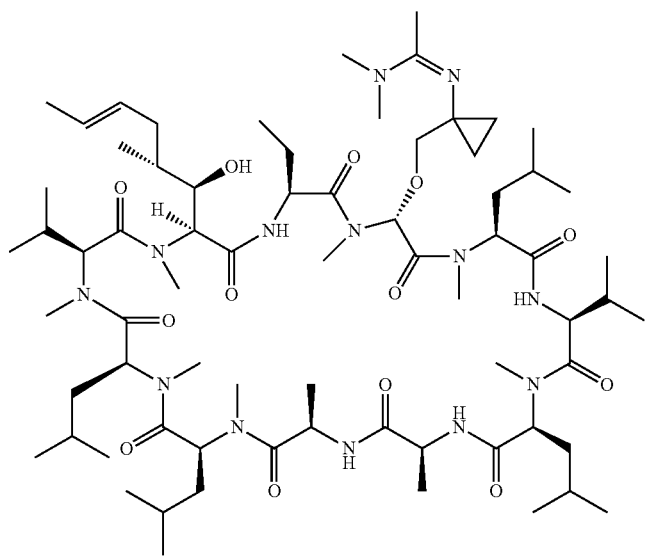

13

Step 3: V (200 mg) and E1 (103 mg) were dissolved in 2 mL MeOH and to this stirred solution was added MgSO$_4$ (2 g). The resultant mixture was stirred at RT. After 16 hours, the mixture was diluted with 10 mL DCM and filtered. The filtrate was concentrated in vacuo to yield 180 mg crude product, which was further purified by chromatography to give compound 13 (($^1$H-NMR (400 MHz CDCl$_3$, δ (ppm)): 5.91, sarcosine residue); H RMS Electrospray (M+1) 1356.8; 1357.7; mass according to isotope distribution: 1355.95 (100%), 1356.96 (75.7%)).

Preparation of Compounds 14 and 15:

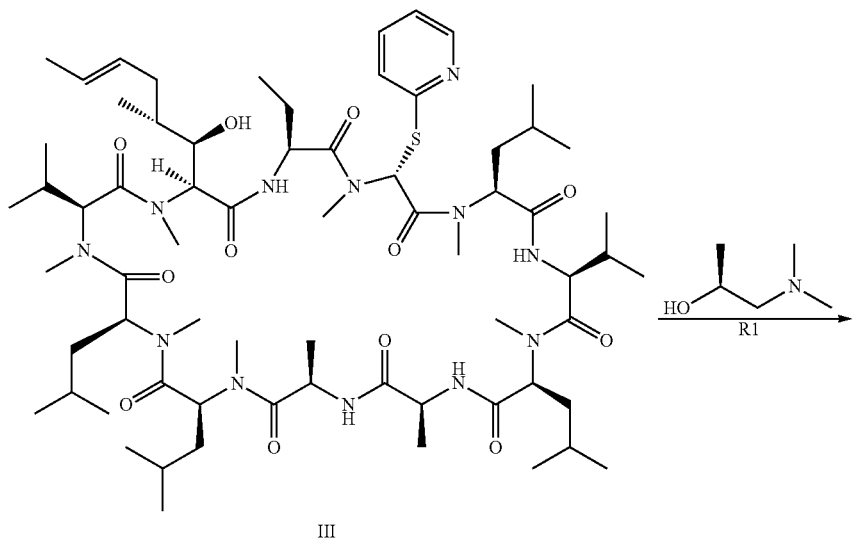

III

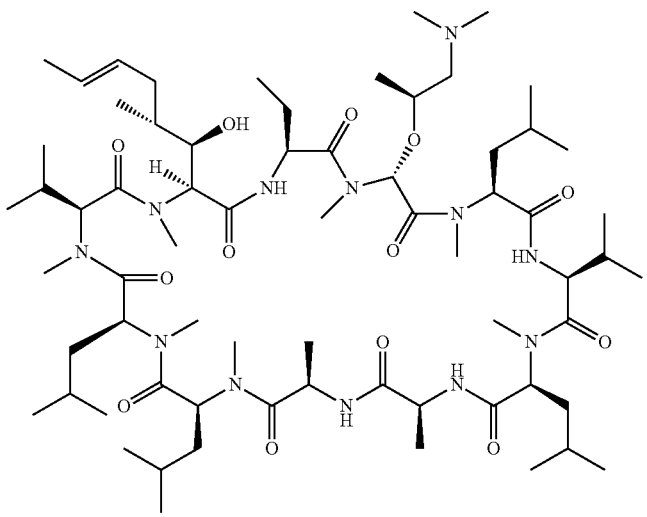

14

Compound 14: To a stirred solution of III (1 g) and R1 (338.2 mg) in 20 mL THF was first added to the flask, Cu(OTf)$_2$ (1 g) at 0° C. under N2, to be followed by TMSCl (198 mg). The mixture was then stirred at RT under N$_2$ for 16 hours. The resulting mixture was poured into 20 mL water, and then 20 mL of i-PrOAc was added. The aqueous phase was adjusted to pH 8.0 by the addition of aq. K$_2$CO$_3$. The aqueous phase was separated and was extracted by another portion of i-PrOAc. The combined organic phase was washed twice with aqueous malic acid solution (840 mg malic acid in 20 mL water). After separation of the phases, the aqueous phase was adjusted to pH 8.0 with the addition of aqueous K$_2$CO$_3$. The aqueous solution was then extracted twice with 20 mL i-PrOAc. The organic phase was dried and concentrated to give 340 mg of the desired compound 14. Compound 14: (($^1$H-NMR (400 MHz CDCl$_3$, δ (ppm)): 6.08, sarcosine residue); HRMS Electrospray (M+1) 1303.7; 1304.6; mass according to isotope distribution: 1302.93 (100%), 1303.93 (72.5%)).

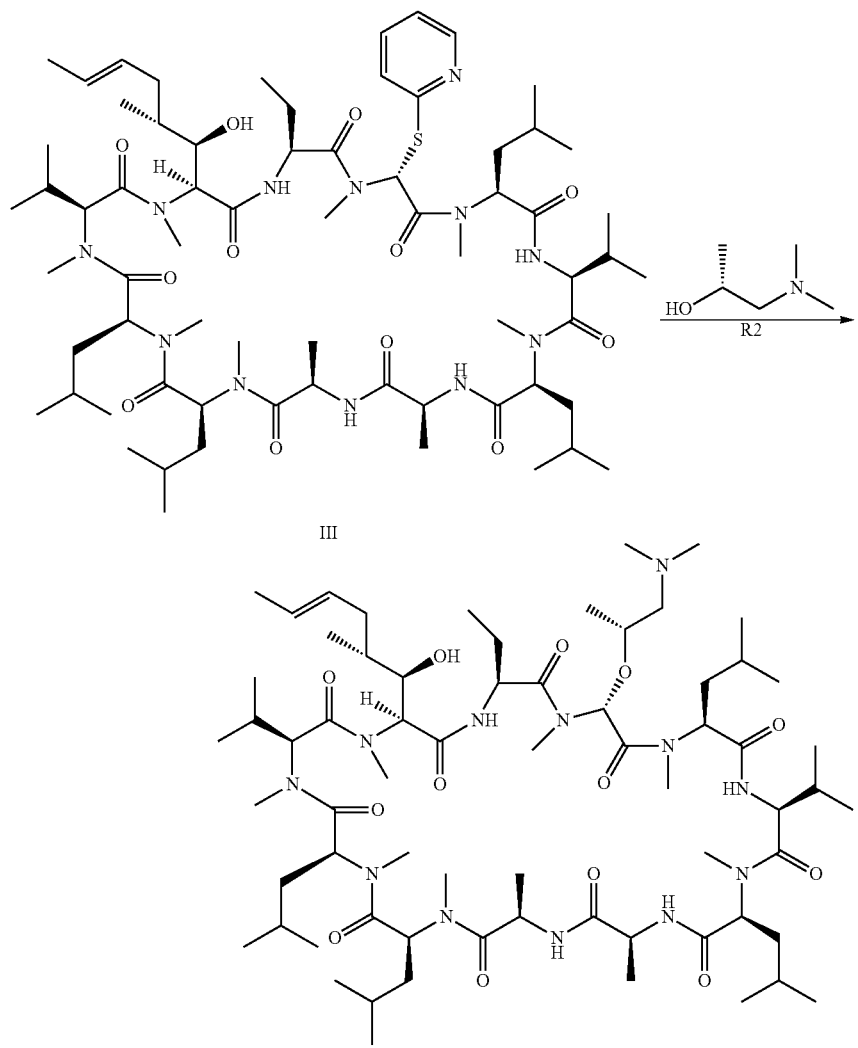

Compound 15 was prepared analogously according to the general method described above for compound 14 from compound III and R2 and obtained after further purification by chromatography. Compound 15 (($^1$H-NMR (400 MHz CDCl$_3$, δ (ppm)): 6.31, sarcosine residue); HRMS Electrospray (M+1) 1303.4, 1304.6; mass according to isotope distribution: 1302.93(100%); 1303.93(72.5%)).

Example 2—Functional and Inhibitional Assays

The compounds as prepared in Example 1 were tested in cyclophilin A and D peptidyl-prolyl isomerase functional assays using human recombinant enzymes (PPIase assay), as well as in a calcineurin inhibition assay with and without cyclophilin A. The compounds were also tested in a calcium retention capacity (CRC) assay in permeabilized HepG2. Cyclosporin A was used as a control in all assays.

The compounds were supplied as a dry powder or oils and made up as a 10 mM stock solution in 100% DMSO. Subsequent dilutions were made in 100% DMSO for use in all assays.

Cyclophilin Peptidyl-Prolyl Isomerase Functional Assay

Measurements were performed using an Agilent 8453 spectrophotometer. Assay buffer was cooled to 10° C. (with stirring) in a precision glass cuvette and inhibitor was added from a DMSO stock solution to afford a final concentration of <1% DMSO. A blank spectrum was obtained and then enzyme and substrate were added and the change in absorbance measured over 5 min. A first order rate was fitted to the absorbance data to obtain a rate constant (first 10 to 15 s were eliminated due to mixing). The catalytic rate was calculated from the enzymatic rate minus the background rate. The enzymatic rate constant, determined in duplicate at each inhibitor concentration, was plotted against inhibitor concentration and a non-linear fit by SigmaPlot generated a $K_i$.

Calcineurin Phosphatase Inhibition Assay With and Without Cyclophilin A

This colorimetric 96 well assay is designed for inhibitor screening of recombinant Calcineurin (CaN). Activity is determined using the RII phosphopeptide substrate, the most efficient and selective peptide known for calcineurin, and detection of free phosphate released is based on the classic malachite green assay. CypA and CsA form a complex which binds CaN/calmodulin, which will inhibit dephosphorylation of the RII peptide. In the presence of recombinant CypA, cyclosporine-like cyclophilin inhibitors were screened in the assay to determine inhibition of calcineurin phosphatase activity. In a 96-well plate, two dilution series were prepared, one with the cyclophilin A enzyme (7-point) and another without (4-point). An assay buffer/calcineurin/calmodulin master mix was added followed by the phosphopeptide substrate (RII). After incubation at 30° C. the reaction was stopped by the addition of malachite green/molybdate reagent. The coloured complex formed with liberated phosphate was quantified by reading the absorbance at 620 nm. The blank corrected data was plotted against inhibitor concentration to determine an $IC_{50}$ value.

Calcium Retention Capacity (CRC) Assay in Permeabilized HepG2

HepG2 cells were permeabilised with 100 μM digitonin for 10 min in ice cold buffer containing 1 mM EGTA. Following two wash steps to remove the digitonin, the cells were plated into 96 well black and clear plates at $1e^6$ cell per well in 180 μL assay buffer containing 0.5 μM Calcium Green 5N. Compounds dilutions were made in DMSO to 1000-fold the final concentration, diluted 1:100 in assay buffer and added to the assay as 20 μL per well. The assay buffer contained 5 mM glutamate and 2.5 mM malate. The cell plate was immediately run on the FLIPR Tetra™ which added 5 μL of 200 μM (5 μM) calcium chloride every 5 minutes whilst reading the plate every 3 seconds. The area under the curve at each concentration of compound was calculated. $EC_{50}$ values were calculated. The use of Area Under the Curve (ALIC) rather than the number of Calcium additions before buffering is lost was determined to be a more accurate way of analysing the data.

The assay results obtained are summarized in the Tables 2-4 below:

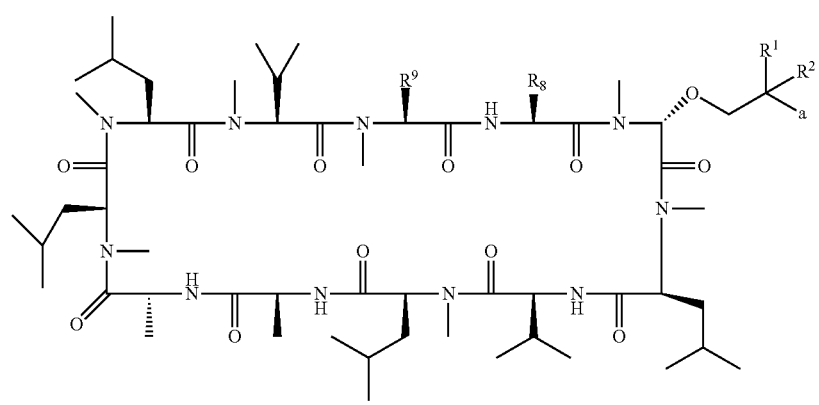

Formula 1

TABLE 2

Cyclophilin Peptidyl-Prolyl Isomerase Functional Assay Results

| Compound | $R^1$ | $R^2$ | A | $R^8$ | $R^9$ | Inhibition ($K_i$, nM) Human CypA | Inhibition ($K_i$, nM) Human CypD |
|---|---|---|---|---|---|---|---|
| CsA | — | — | — | — | — | 7.8 | 9.1 |
| 1 (Ref.) | H | H | —N(CH₃)₂ | —CH₂CH₃ | | 4.1 | 12 |
| 2 | H | H | —N(CH₃)₂ | —CH(OH)CH₃ | | 50 | 78 |
| 3 | H | H | —N(CH₃)₂ | —CH(CH₃)₂ | | 5.2 | 5.1 |

TABLE 2-continued

Cyclophilin Peptidyl-Prolyl Isomerase Functional Assay Results

| Compound | $R^1$ | $R^2$ | A | $R^8$ | $R^9$ | Inhibition ($K_i$, nM) Human CypA | Inhibition ($K_i$, nM) Human CypD |
|---|---|---|---|---|---|---|---|
| 4 | H | H | morpholine (N-linked) | —CH(CH$_3$)$_2$ | CH=CH-CH$_3$ with HO and CH$_3$ substituents | 2.3 | 4.1 |
| 5 | H | H | —N(CH$_3$)$_2$ | —CH(CH$_3$)$_2$ | ketone with CH=CH-CH$_3$ and CH$_3$ | 23 | 17 |
| 6 | H | H | morpholine (N-linked) | —CH(CH$_3$)$_2$ | ketone with CH=CH-CH$_3$ and CH$_3$ | 90 | 150 |
| 7 | H | H | —N(CH$_3$)$_2$ | —CH$_2$CH$_2$CH$_3$ | CH=CH-CH$_3$ with HO and CH$_3$ | 9.4 | 5.9 |
| 8 | H | H | morpholine (N-linked) | —CH$_2$CH$_2$CH$_3$ | CH=CH-CH$_3$ with HO and CH$_3$ | 39 | 35 |
| 9 | H | H | —N=C(CH$_3$)N(CH$_3$)$_2$ | —CH$_2$CH$_3$ | CH=CH-CH$_3$ with HO and CH$_3$ | 11 | 8.2 |
| 10 | H | H | —N=C(H)N(CH$_3$)$_2$ | —CH$_2$CH$_3$ | CH=CH-CH$_3$ with HO and CH$_3$ | 14 | 9.7 |
| 11 | CH$_3$ | CH$_3$ | —N(CH$_3$)$_2$ | —CH$_2$CH$_3$ | CH=CH-CH$_3$ with HO and CH$_3$ | 25 | 6 |
| 12 | —CH$_2$— | —CH$_2$— | —N(CH$_3$)$_2$ | —CH$_2$CH$_3$ | CH=CH-CH$_3$ with HO and CH$_3$ | 6.5 | 6 |

TABLE 3

Calcineurin Phosphatase Inhibition Assay With and Without Cyclophilin A - Results

| Compound | R¹ | R² | A | R⁸ | R⁹ | CaN Inhibition (IC$_{50}$, nM) + CypA | CaN Inhibition (IC$_{50}$, nM) − CypA |
|---|---|---|---|---|---|---|---|
| CsA | — | — | — | — | — | 107 | >10000 |
| 1 (Ref.) | H | H | —N(CH$_3$)$_2$ | —CH$_2$CH$_3$ | *(HO, alkene substituent)* | 1551 | 2276 |
| 2 | H | H | —N(CH$_3$)$_2$ | —CH(OH)CH$_3$ | *(HO, alkene substituent)* | 5002 | >10000 |
| 3 | H | H | —N(CH$_3$)$_2$ | —CH(CH$_3$)$_2$ | *(HO, alkene substituent)* | 1320 | 5508 |
| 4 | H | H | *(morpholino)* | —CH(CH$_3$)$_2$ | *(HO, alkene substituent)* | 1325 | 4193 |
| 5 | H | H | —N(CH$_3$)$_2$ | —CH(CH$_3$)$_2$ | *(ketone, alkene substituent)* | >10000 | >10000 |
| 6 | H | H | *(morpholino)* | —CH(CH$_3$)$_2$ | *(ketone, alkene substituent)* | >10000 | >10000 |
| 7 | H | H | —N(CH$_3$)$_2$ | —CH$_2$CH$_2$CH$_3$ | *(HO, alkene substituent)* | 789 | 3220 |
| 8 | H | H | *(morpholino)* | —CH$_2$CH$_2$CH$_3$ | *(HO, alkene substituent)* | 636.4 | 7828 |
| 9 | H | H | —N=C(CH$_3$)N(CH$_3$)$_2$ | —CH$_2$CH$_3$ | *(HO, alkene substituent)* | 2022 | 3882 |

TABLE 3-continued

Calcineurin Phosphatase Inhibition Assay With and Without Cyclophilin A - Results

| Compound | R¹ | R² | A | R⁸ | R⁹ | CaN Inhibition (IC$_{50}$, nM) + CypA | CaN Inhibition (IC$_{50}$, nM) − CypA |
|---|---|---|---|---|---|---|---|
| 10 | H | H | —N=C(H)N(CH$_3$)$_2$ | —CH$_2$CH$_3$ | *(structure)* | 1827 | 3705 |
| 11 | CH$_3$ | CH$_3$ | —N(CH$_3$)$_2$ | —CH$_2$CH$_3$ | *(structure)* | 615.9 | 1623 |
| 12 | —CH$_2$— | —CH$_2$— | —N(CH$_3$)$_2$ | —CH$_2$CH$_3$ | *(structure)* | n.d. | n.d. |

TABLE 4

Calcium Retention Capacity (CRC) Assay in permeabilized HepG2 - Results

| Compound | R¹ | R² | A | R⁸ | R⁹ | Calcium Retention Capacity EC$_{50}$ (nM) |
|---|---|---|---|---|---|---|
| CsA | — | — | — | — | — | 369 |
| 1 (Ref.) | H | H | —N(CH$_3$)$_2$ | —CH$_2$CH$_3$ | *(structure)* | 916 |
| 2 | H | H | —N(CH$_3$)$_2$ | —CH(OH)CH$_3$ | *(structure)* | >10000 |
| 3 | H | H | —N(CH$_3$)$_2$ | —CH(CH$_3$)$_2$ | *(structure)* | 946 |
| 4 | H | H | *(morpholine)* | —CH(CH$_3$)$_2$ | *(structure)* | 320 |

TABLE 4-continued

Calcium Retention Capacity (CRC) Assay in permeabilized HepG2 - Results

| Compound | R¹ | R² | A | R⁸ | R⁹ | Calcium Retention Capacity EC$_{50}$ (nM) |
|---|---|---|---|---|---|---|
| 5 | H | H | —N(CH$_3$)$_2$ | —CH(CH$_3$)$_2$ | (ketone-containing alkenyl group) | >10000 |
| 6 | H | H | morpholinyl | —CH(CH$_3$)$_2$ | (ketone-containing alkenyl group) | >10000 |
| 7 | H | H | —N(CH$_3$)$_2$ | —CH$_2$CH$_2$CH$_3$ | (hydroxy-containing alkenyl group) | 2372 |
| 8 | H | H | morpholinyl | —CH$_2$CH$_2$CH$_3$ | (hydroxy-containing alkenyl group) | 1609 |
| 9 | H | H | —N=C(CH$_2$)N(CH$_3$)$_2$ | —CH$_2$CH$_3$ | (hydroxy-containing alkenyl group) | 468 |
| 10 | H | H | —N=C(H)N(CH$_3$)$_2$ | —CH$_2$CH$_3$ | (hydroxy-containing alkenyl group) | 3201 |
| 11 | CH$_3$ | CH$_3$ | —N(CH$_3$)$_2$ | —CH$_2$CH$_3$ | (hydroxy-containing alkenyl group) | 3318 |
| 12 | —CH$_2$— | —CH$_2$— | —N(CH$_3$)$_2$ | —CH$_2$CH$_3$ | (hydroxy-containing alkenyl group) | n.d. |

It was observed (ref. Table 2) that the tested compounds have unexpectedly high levels of human cyclophilin inhibition, in particularly inhibition of human cyclophilin D, compared to the cyclosporin A control, and also at levels comparable to reference compound 1. It was further observed (ref. Table 3), that calcineurin inhibition activity of the tested compounds in the presence of cyclophilin A was lower compared to the cyclosporin A control and in some cases the reference Compound 1.

The binding to cyclophilin A and inhibition of calcineurin is closely linked to immunosuppression. Without wishing to be bound by theory, it is believed that the prevention or treatment of cell injury or death, e.g. cell necrosis and associated diseases or conditions, which are driven by inflammation processes may be better achieved by compounds having potent anti-inflammatory activity but lower immunosuppressive activity, such as characterized by decreased affinity for binding to cyclophilin A and calcineurin.

In particular, it is believed that higher level of inhibition of especially of cyclophilin D, which regulates the opening of the mitochondrial permeability transition pore (PTP) may lead to improved prevention and/or treatment of cell injury or cell death and accordingly, in the prevention or treatment of conditions or diseases associated with mitochondria dysfunction.

The calcium retention capacity (CRC) assay is a model for mitochondrial function, based on the inhibition of opening of the mitochondrial permeability transition pore. Ca++ overload over a sustained period of time is understood to trigger prolonged PTP opening and mitochondrial dysfunction, leading to cell death. The assay as described above measures the loss of inhibition based on the release of calcium, which is determined by increased intensity of fluorescence reporting of the calcium-binding dye used in the assay. It was observed that some of the compounds tested have significantly increased calcium retention capacity compared to the cyclosporin A control, and were comparable, or in some cases, demonstrated to have improved capacity over the reference compound 1.

The invention claimed is:

1. A compound, wherein the compound, or pharmaceutically acceptable salt thereof is:

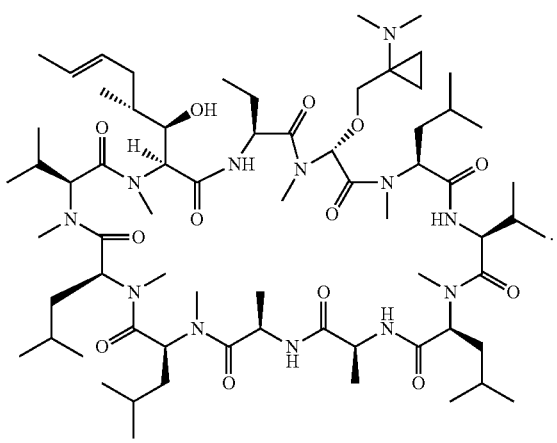 [SMILES: C/C=C/C[C@@H](C)[C@@H](O)[C@H]1C(=O)N[C@@H](CC)C(=O)N(C)[C@H](OCC2(N(C)C)CC2)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

2. A compound, wherein the compound, or pharmaceutically acceptable salt thereof is:

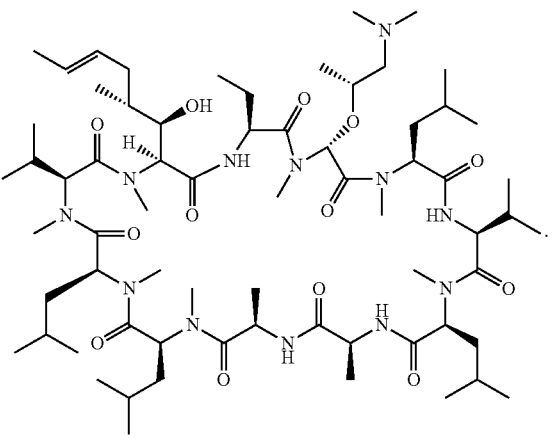 [SMILES: C/C=C/C[C@@H](C)[C@@H](O)[C@H]1C(=O)N[C@@H](CC)C(=O)N(C)[C@H](O[C@H](C)CN(C)C)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

3. A compound, wherein the compound, or pharmaceutically acceptable salt thereof is:

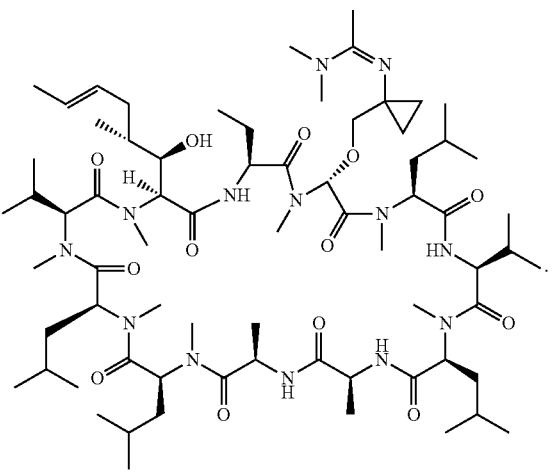 [SMILES: C/C=C/C[C@@H](C)[C@@H](O)[C@H]1C(=O)N[C@@H](CC)C(=O)N(C)[C@H](OCC2(/N=C(/C)N(C)C)CC2)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

* * * * *